US010227313B2

(12) United States Patent
Gupta et al.

(10) Patent No.: US 10,227,313 B2
(45) Date of Patent: Mar. 12, 2019

(54) PROCESS FOR MAKING BENZOXAZINES

(71) Applicant: CYTEC INDUSTRIES INC., Woodland Park, NJ (US)

(72) Inventors: Ram B. Gupta, Stamford, CT (US); Manav Gupta, Karnataka (IN)

(73) Assignee: CYTEC INDUSTRIES INC., Woodland Park, NJ (US)

( * ) Notice: Subject to any disclaimer, the term of this patent is extended or adjusted under 35 U.S.C. 154(b) by 0 days.

(21) Appl. No.: 15/868,848

(22) Filed: Jan. 11, 2018

(65) Prior Publication Data

US 2018/0127387 A1    May 10, 2018

Related U.S. Application Data

(62) Division of application No. 14/919,186, filed on Oct. 21, 2015, now Pat. No. 9,902,706.

(60) Provisional application No. 62/068,806, filed on Oct. 27, 2014.

(51) Int. Cl.

| *C07D 265/16* | (2006.01) |
|---|---|
| *C07D 413/10* | (2006.01) |
| *C07D 413/14* | (2006.01) |
| *C07C 315/04* | (2006.01) |
| *C07C 317/36* | (2006.01) |

(52) U.S. Cl.
CPC .......... *C07D 265/16* (2013.01); *C07C 315/04* (2013.01); *C07C 317/36* (2013.01); *C07D 413/10* (2013.01); *C07D 413/14* (2013.01)

(58) Field of Classification Search
CPC .. C07D 265/16; C07D 413/10; C07D 413/14; C07C 315/04; C07C 317/36
USPC ........................................................ 544/90
See application file for complete search history.

(56) References Cited

U.S. PATENT DOCUMENTS

| 2,354,784 | A | 8/1944 | Tschesche et al. |
|---|---|---|---|
| 2,826,577 | A | 3/1958 | Rigterink |
| 5,543,516 | A | 8/1996 | Ishida |
| 6,160,079 | A | 12/2000 | Ishida et al. |
| 6,225,440 | B1 | 5/2001 | Ishida |
| 6,620,905 | B1 | 9/2003 | Musa |
| 7,795,359 | B2 | 9/2010 | Devlin et al. |
| 7,947,802 | B2 | 5/2011 | Ishida et al. |
| 2007/0275285 | A1 | 11/2007 | Choi et al. |
| 2008/0045688 | A1 | 2/2008 | Lin et al. |
| 2009/0270615 | A1 | 10/2009 | Taden et al. |
| 2010/0140542 | A1 | 6/2010 | Ji et al. |
| 2010/0330287 | A1 | 12/2010 | Tietze et al. |
| 2011/0172356 | A1 | 7/2011 | Kreiling et al. |

FOREIGN PATENT DOCUMENTS

| CN | 101265255 A | 9/2008 |
|---|---|---|
| WO | 2000000535 | 1/2000 |
| WO | 2000061650 | 10/2000 |
| WO | 2007064801 | 6/2007 |

OTHER PUBLICATIONS

Agag, et al., A New Synthetic Approach for Difficult Benzoxazines: Preparation and Polymerization of 4,4'-Diaminodiphenyl Sulfone-Based Benzoxazine Monomer; Polymer, vol. 50 (2009), p. 5940-5944.
Andreu, et al., Carboxylic Acid-Containing Benzoxazines as Efficient Catalysts in the Thermal Polymerization of Benzoxazines, Journal of Polymer Science, Part A; Polymer Chemistry, vol. 46, (2008).
Andreu, et al., Synthesis of Novel Benzoxazines Containing Glycidyl Groups: A Study of the Crosslinking Behavior, Journal of Polymer Science, Part A; Polymer Chemistry, vol. 44, (2006).
Lin et al., Aromatic Diamine-Based Benzoxazines and Their High Performance Thermosets, Polymer, vol. 49, (2008).
Garcia et al., Recyclable, Strong Thermosets and Organogels via Paraformaldehyde Condensation with Diamines, Science vol. 344 (2014).
Giumanini et al., High Yield Synthesis of 1,3,5-Triphenylhexahydro-Sym-triazine and its X-Ray Crystal Structure Determination, Journal fur. prakt. Chemie, vol. 327 (1985).
Ishida et al., Benzoxazine Chemistry in Solution and Melt, "Handbook of Benzoxazine Resins" 2011, Elsevier publication.
Chang et al., Facile, One-Pot Synthesis of Aromativ Diamine-Based Benzoxazines and Their Advantages Over Diamines as Epoxy Hardeners, Journal of Polymer Science, Part A; Polymer chemistry (2010).
Brunovska et al., 1.3.5-Triphenylhexaphydro-1,3,5-Triazine—Active Intermediate and Precursor in the Novel Synthesis of Benzoxazine Monomers and Oligomers, Macromol. Chem. Phys. vol. 200 (1999).
Xiaoying Wang et al: "Influence of electronic effects from bridging groups on synthetic reaction and thermally activated polymerization of bisphenol-based benzoxazines", Journal of Polymer Science Part A: Polymer Chemistry, vol. 49, No. 6, Mar. 15, 2011 (Mar. 15, 2011).
Liu Yanfang et al: "The polymerization behavior and thermal properties of benzoxazine based ono-allylphenol and 4,4'-diaminodiphenyl met", Reactive & Functional Polymers, Elsevier Science Publishers BV, NL, vol. 75, Dec. 9, 2013 (Dec. 19, 2013).
International Search Report. PCT/US2015/056802. dated Dec. 22, 2015.

*Primary Examiner* — Kahsay Habte
(74) *Attorney, Agent, or Firm* — Thi Dang

(57) ABSTRACT

A synthesis process for making a benzoxazine compound containing at least one benzoxazine unit from aromatic amine containing at least one primary amino group, at least one phenolic compound with at least one ortho-hydrogen, and alkyl formcel. In one embodiment, the aromatic amine is reacted with alkyl formcel to generate an alkoxymethyl intermediate compound. Subsequently, the intermediate compound is reacted with a phenol to generate the benzoxazine compound. In another embodiment, the benzoxazine compound is formed by reacting aromatic amine with alkyl formcel and phenol in one reaction step. Also disclosed is a method for isolating the alkoxymethyl compound formed by (Continued)

reacting aromatic amine with alkyl formcel. The isolated alkoxymethyl compound is useful as a reactant in a subsequent reaction.

2 Claims, 1 Drawing Sheet

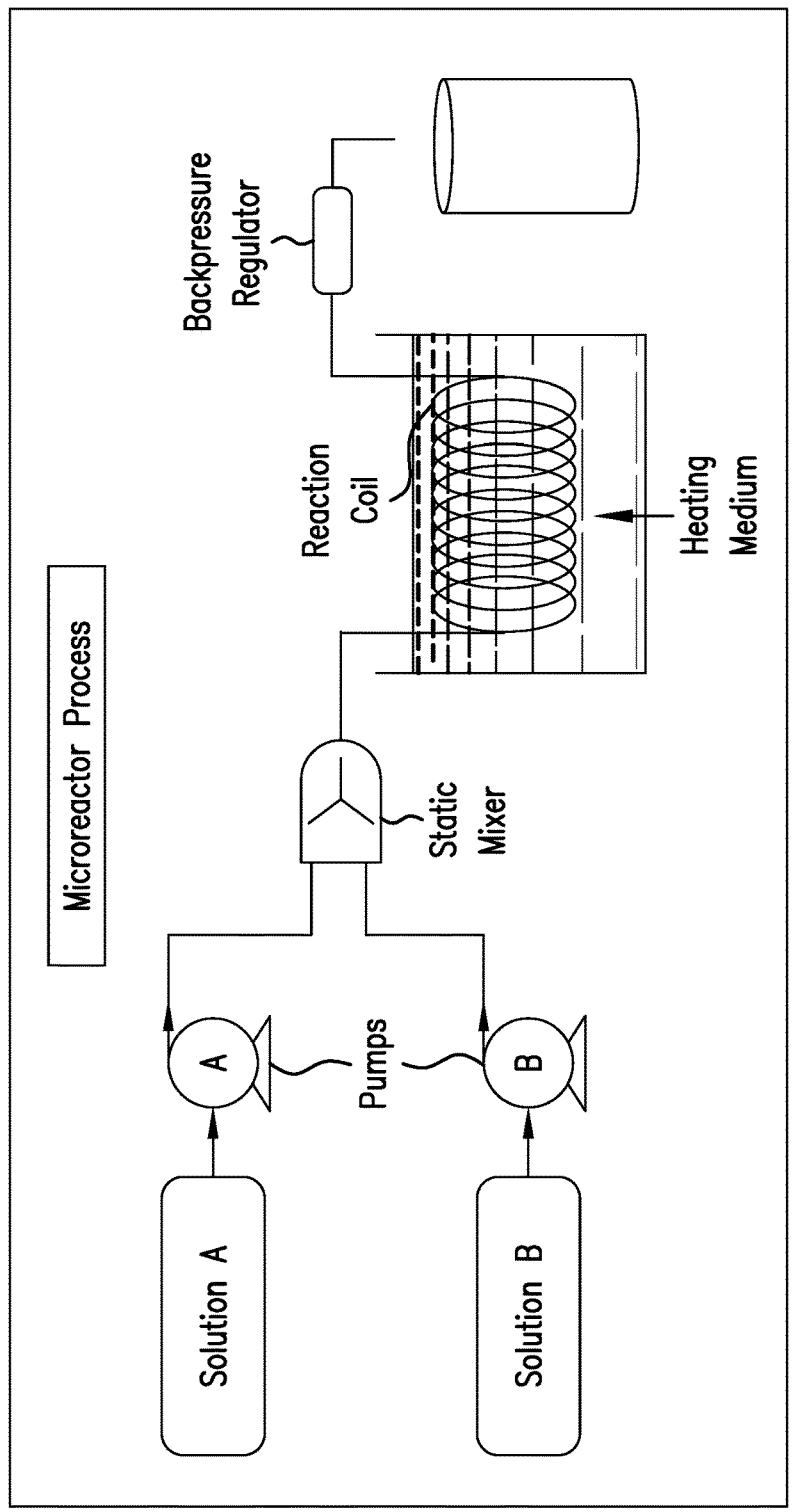

PROCESS FOR MAKING BENZOXAZINES

The instant application is a divisional application of U.S. application Ser. No. 14/919,186 filed on Oct. 21, 2015, which claims the benefit of U.S. Provisional Patent Application No. 62/068,806 filed on Oct. 27, 2014, both of which are incorporated by reference in their entirety.

Benzoxazines are an important class of thermosetting resins. This class of compounds has generated significant interest as an alternative to phenolic, epoxy, bismaleimides and other thermosetting resins in several application areas, including aerospace and automotive industries, mainly due to a number of advantages offered by these resins. These advantages include relatively long shelf-life, molecular design flexibility, low cost, high glass transition temperature ($T_g$), high modulus, relatively low viscosities, good flame retardant properties, low moisture absorption, no by-products released during curing and very low shrinkage upon curing. Furthermore, benzoxazines are capable of being self-cured upon heating; i.e. there is no need for an additional curing agent. In addition, the aromatic amines based benzoxazines offer an additional site on the aromatic amine to build the polybenzoxazine's molecular weight and/or to provide crosslinking sites.

Conventional approaches for synthesizing benzoxazines have limited success, thus, there remains a commercial need for an efficient method for producing benzoxazines at a commercial scale.

BRIEF DESCRIPTION OF THE DRAWING

The drawing FIGURE schematically illustrates a microreactor system for carrying out the benzoxazine synthesis in according to an embodiment of the present disclosure.

DETAILED DESCRIPTION

Benzoxazines can be synthesized by reacting an amine with excess of paraformaldehyde and phenol. One approach is a solventless method as disclosed in U.S. Pat. No. 5,543,516, where the amine, paraformaldehyde and phenols are mixed together and heated in the absence of any solvent to form the benzoxazine.

The widely accepted mechanism for the formation of benzoxazine occurs in two steps as shown in Scheme 1 below.

Scheme 1

Step 1:

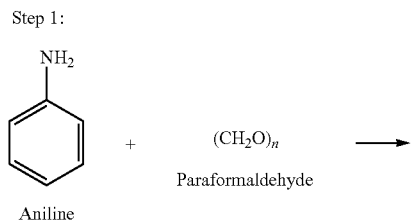

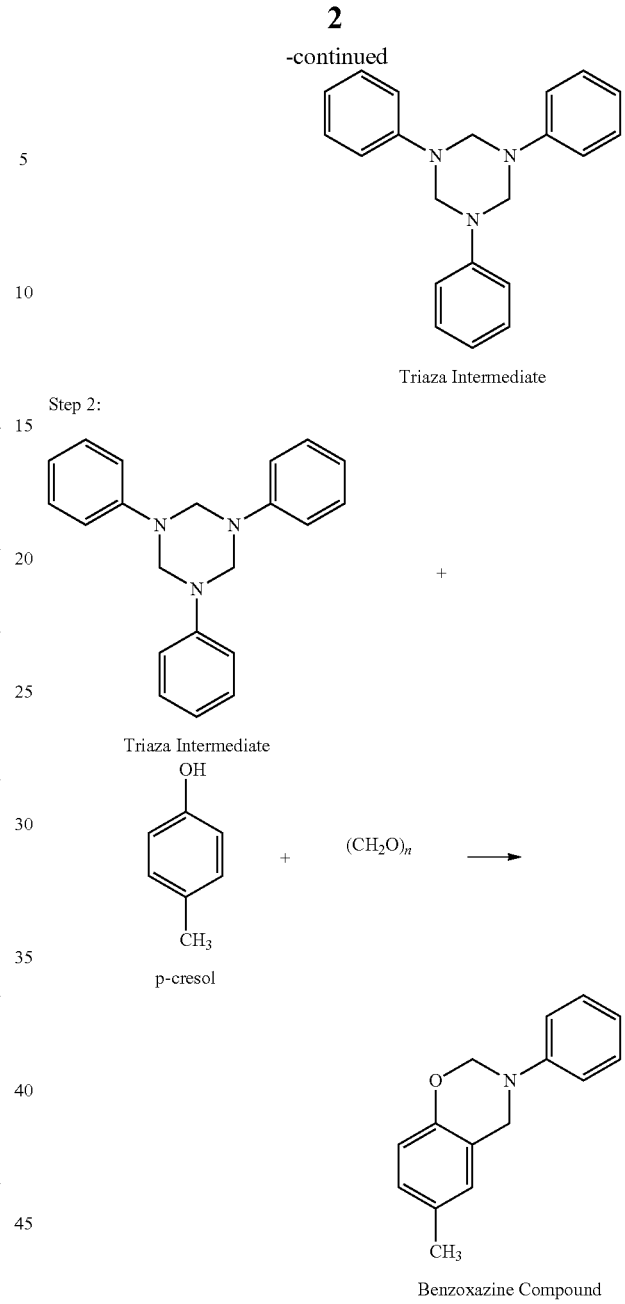

In the first step, the amine reacts with paraformaldehyde to form the hexahydrotriazine structure (also called triaza intermediate). And in the second step, this intermediate reacts with phenol and paraformaldehyde to generate the benzoxazine structure. This mechanism can be established by actually isolating the triaza intermediate and then further reacting the isolated triaza intermediate with meta-cresol to form the benzoxazine shown in Scheme 1 (see, for example, Macromol. Chem. Phys. 200, 1745 (1999); Angelo G. Giumanini, and Giancarlo Verardo, Journal fur. prakt. Chemie, Vol 327, page 739 (1985); R. Andreu, J. A. Reina and J. C. Honda, Journal of Polymer Science, Part A; Polymer Chemistry, Vol. 46, page 3353 (2008); R. Andreu, M. A. Espinosa, M. Galia, V. Cadiz, J. C. Ronda and J. A. Reina, Journal of Polymer Science, Part A; Polymer Chemistry, Vol. 44, page 1529 (2006); R. Andreu, J. A. Reina and J. C. Ronda Journal of Polymer Science, Part A; Polymer chemistry, page 6091 (2008)).

A vast majority of benzoxazines used for thermoset applications has been based on monofunctional aromatic amines and difunctional phenols (or bisphenols). A wide variety of available bisphenols offer great opportunities in molecular design to tailor polybenzoxazines for specialty application. However, only a few number of monomers derived from difunctional aromatic amine (or aromatic diamine) and monofunctional phenols have been reported in spite of the fact that a vast number of aromatic diamines and monophenols are commercially available. The reason, as reported in literature, has been the formation of a stable process. Handling of this phase separated solids add further difficulties" (Hatsuo Ishida and Jin-Ping Liu, Chapter 2, page 86 in "Handbook of Benzoxazine Resins" Edited by Hatsuo Ishida and Tarek Agag, 2011, Elsevier publication.

Thus, it is no surprise that if an aromatic diamine is used as a substrate, it leads to the formation of polymeric hexahydrotriazine structures as reported in Jeannette et al., Science vol. 344, page 732 (2014), where a recyclable thermoset hexahydrotriazine polymer is prepared from the condensation of 4,4'-oxydianiline and paraformaldehyde, as shown in Scheme 2 below.

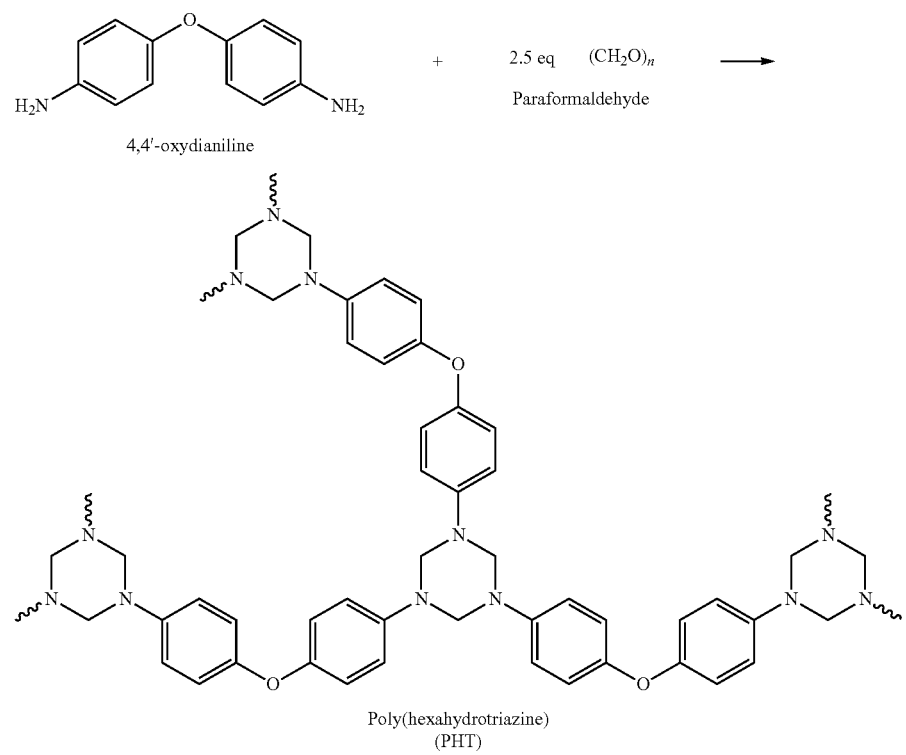

triaza network formed from the condensation of aromatic diamines and formaldehyde which suppresses reaction with phenol to continue for benzoxazine formation. Such triaza network is often times insoluble gel. In addition, other side condensation reactions are possible as disclosed in Tarek Agag, Lin Jin, Hatsuo Ishida, Polymer, 50 (2009), page 5940-5944. It has been noted that a successful synthesis of aromatic diamine-based benzoxazines with the large varieties of commercially available aromatic diamines could increase the molecular design flexibility of benzoxazines, and hence, expand their application.

Ishida and Liu also noted that "the intermediate triaza ring can be particularly problematic, when relatively insoluble diamines, such as aromatic diamines, are used as it forms precipitates with near infinite molecular weight. Thus, the breakup of this precipitated solid becomes the rate limiting There have been recent reports to solve the problem of forming benzoxazines with aromatic diamines. In one approach, as reported in the article by Ching Hsuan Lin, Sheng Lung Chang, Chau Wei Hsieh, Hao Hsin Lee, Polymer, 49, 1220 (2008), the bis-benzoxazine structures from aromatic diamines are made in three steps as shown in Scheme 3 below: first by reacting ortho-hydroxybenzaldehyde with aromatic diamine in DMF solvent to generate the diimine structure which is isolated, and then reduced with NaBH4 and ethanol. In the final step, the resulting diamine dihydroxy compound is reacted with formaldehyde in chloroform to form the final bis-benzoxazine structure.

This process involves three steps, and has limited scope since it requires a variety of substituted ortho-hydroxybenzaldehyde to synthesize different benzoxazines with substitution in the phenolic ring; however, the substituted ortho-hydroxybenzaldehyde compounds are not readily available on a commercial scale.

Scheme 3

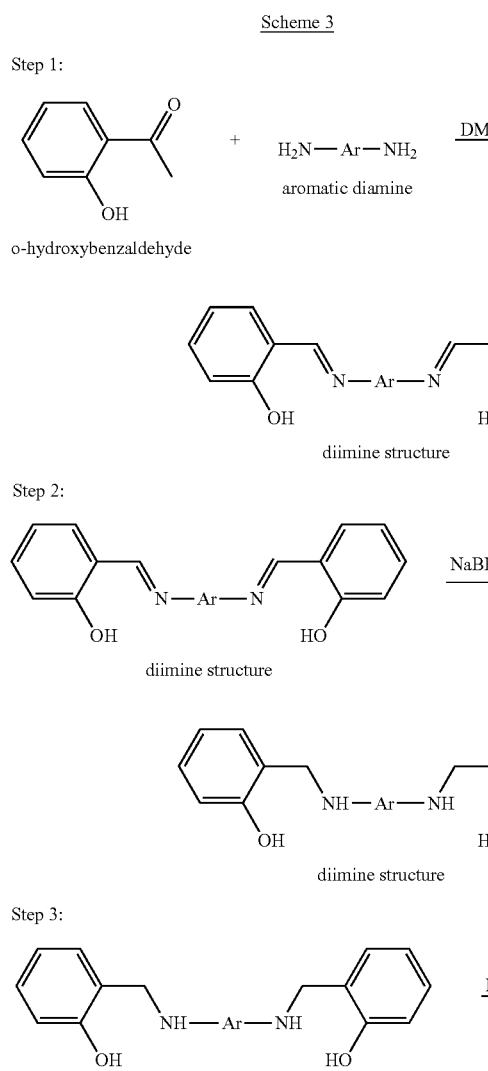

Scheme 4

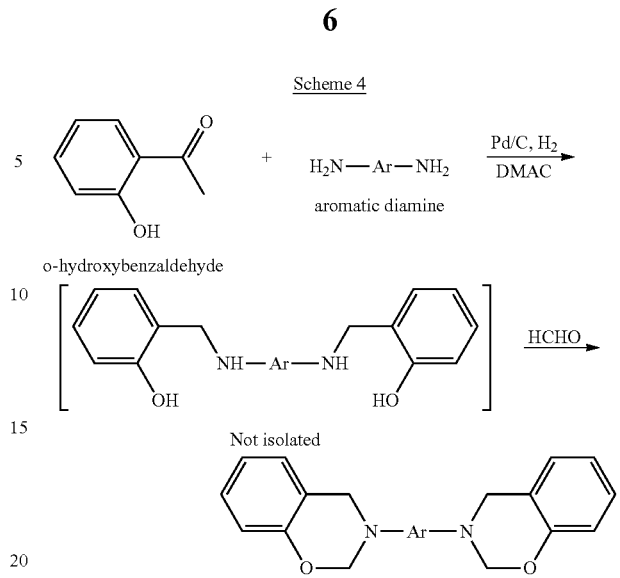

More recently, the above process has been improved as reported by Sheng Lung Chang and Ching Hsuan Lin, Journal of Polymer Science, Part A; Polymer chemistry, page 2430 (2010), where the ortho-hydroxybenzaldehyde is reacted with the diamine under reductive conditions in DMAC solvent and Pd/C-hydrogen for reduction (Scheme 4 below). The resulting diamine without isolation is reacted with formaldehyde to form the bisbenzoxazine from aromatic diamine. This is an improvement over the preceding process as a one-pot process, but again has the limited scope since the required substituted ortho-hydroxybenzaldehyde compounds for synthesizing different benzoxazines with substitution in phenolic ring are not readily available on a commercial scale.

In yet another approach, the reaction of an aromatic diamine, phenol and paraformaldehyde is carried out in a non-polar solvent, such as xylenes, at high temperature as reported in the journal Polymer, 50, 5940 (2009). However, this process still results in insoluble poly(triaza) structure and the problem of formation of insoluble triaza network as an intermediate in the synthesis of benzoxazines is not completely addressed.

The above approaches have limited success, thus, there is still a commercial need for an efficient synthesis method for producing benzoxazine based on aromatic diamines and phenols which can increase the number of available benzoxazines resins and expand the thermoset applications thereof. The present disclosure offers a solution to the problems associated with benzoxazine synthesis.

In view of the prior art discussed above, it has been determined that the root cause of the problems associated with benzoxazine preparation from the aromatic diamine is the formation of insoluble intermediate hexahydrotriazine (triaza) derivative. It has now been surprisingly discovered that the formation of intermediate hexahydrotriazine (triaza) derivative can be almost eliminated. The present disclosure pertains to a new process for making benzoxazines without the intermediacy of hexahydrotriazine (triaza) derivative. It has been discovered that the reaction of aromatic amines with alkyl formcel instead of paraformaldehyde or formalin, as traditionally practiced in the art, leads to the formation of N-methoxymethyl and its analog intermediates, which have lower molecular weight and higher solubility than hexahydrotriazine (triaza) intermediate that can effectively react further with phenols to successfully form the benzoxazine compound as a final reaction product. In this new process, the formation of hexahydrotriazine (triaza) derivative is not observed. Consequently, this process provides economic advantages in manufacturing cost, and moreover, it can be applied to all aromatic mono-amines, aromatic diamines or aromatic polyamines, thus, opening access to a wide variety of benzoxazines on a commercial scale.

The synthesis of benzoxazines according to the present disclosure includes the reaction of an aromatic amine containing at least one primary amino group with alkyl formcel and at least one phenolic compound. The benzoxazine reaction product derived from the reaction is a compound containing at least one benzoxazine unit (which includes an oxazine ring pendant to a benzene ring). The benzoxazine compounds that can be synthesized include monofunctional and multifunctional benzoxazine monomers and oligomers.

According to one embodiment of the present disclosure, the benzoxazine compound is formed by first reacting an aromatic amine with alkyl formcel to generate an alkoxymethyl intermediate compound. Subsequently, the intermediate compound is reacted with a phenol containing at least one hydrogen ortho to OH group to generate the benzoxazine compound.

In an alternative embodiment, the benzoxazine compound is formed by mixing the aromatic amine, the alkyl formcel, and the phenol, and simultaneously reacting by heating the resulting mixture to affect a reaction.

Aromatic Amines

In some embodiments, the aromatic amine includes the following general structures represented by Formulas I, II and III:

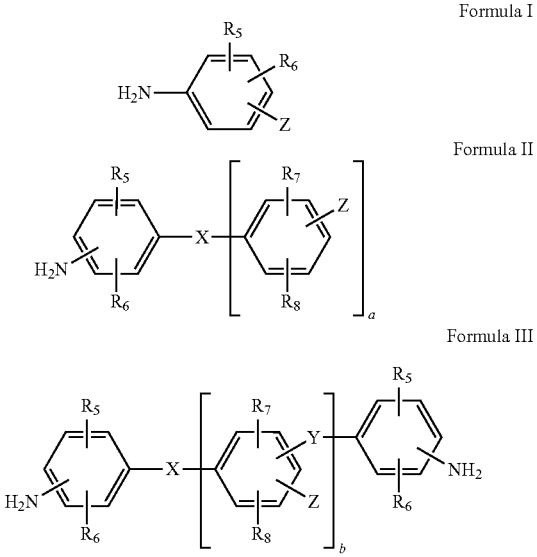

wherein a=1 or 2; and b=0-50;

in Formula III, X and Y are linking groups that are independently selected from a direct bond, O, S, $SO_2$, P=O, (Ph)P=O, OP(=O)O, C=O, substituted or unsubstituted alkylene, substituted or unsubstituted alkylidene, oxoalkylene, substituted or unsubstituted cycloaliphatic or aromatic group, where Ph is phenyl; Z is H or $NH_2$; $R_5$, $R_6$, $R_7$ and $R_8$ are same or different and are independently selected from hydrogen, halogen, substituted or unsubstituted alkyl, alkenyl, alkynyl or alkoxy of C1 to C20 carbon atoms, carboxyl, cyano, aryl, aralkyl or aryloxy group, and optionally, $R_5$ and $R_6$ taken together and/or $R_7$ and $R_8$ taken together being a part of a saturated or unsaturated fused carbocyclic ring, which optionally contains O, N or S atoms in the ring;

in Formula II, when a=1, X is as defined for Formula III, and when a=2, X is one of the following:

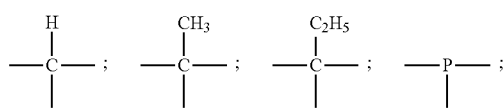

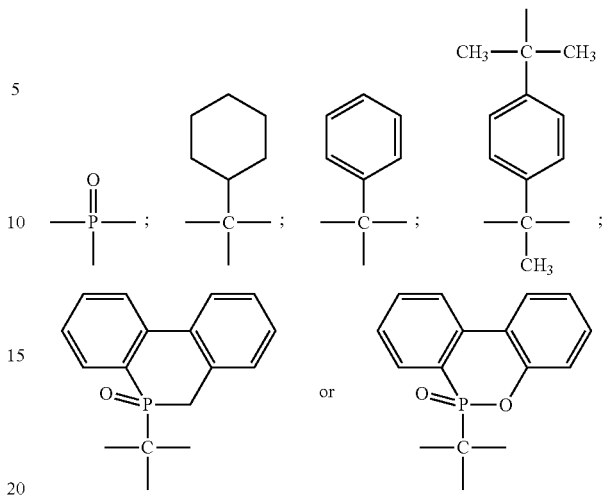

Suitable aromatic amines include monoamines as well as polyamines. Examples of aromatic monoamines include:

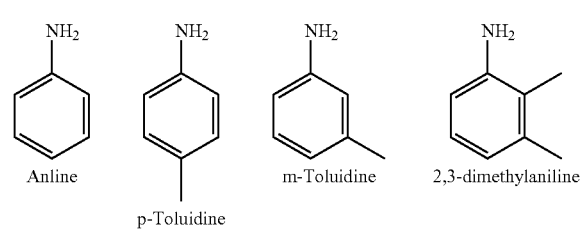

Anline    p-Toluidine    m-Toluidine    2,3-dimethylaniline

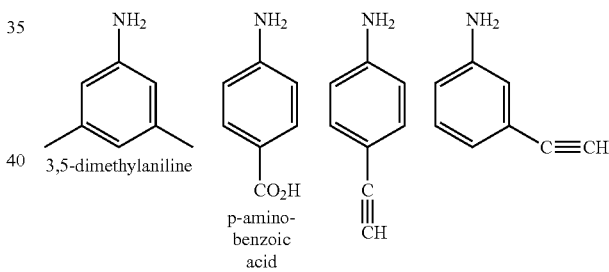

3,5-dimethylaniline    p-aminobenzoic acid

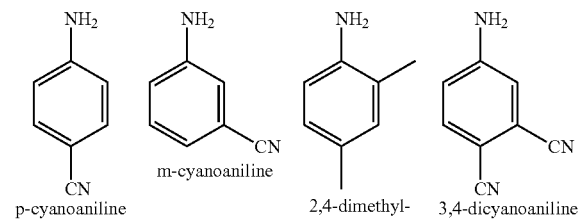

p-cyanoaniline    m-cyanoaniline    2,4-dimethylaniline    3,4-dicyanoaniline

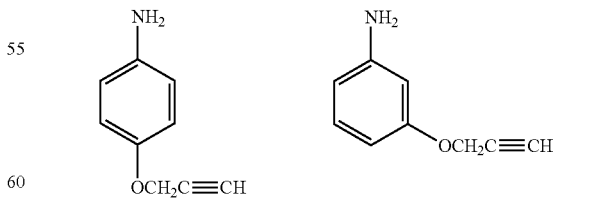

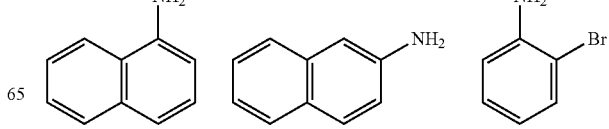

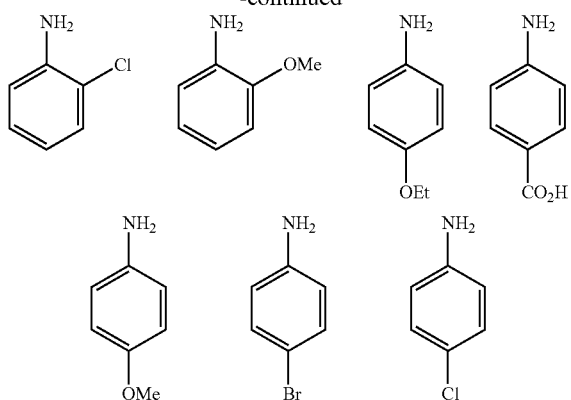
Examples of aromatic diamines include:
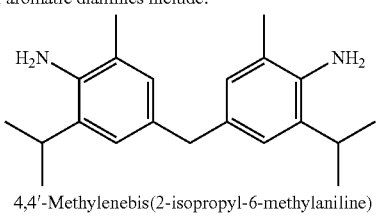
4,4′-Methylenebis(2-isopropyl-6-methylaniline)
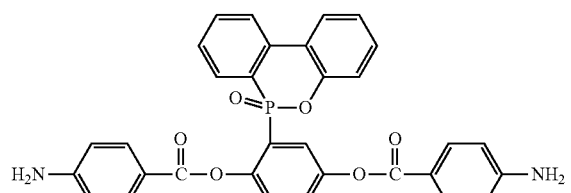
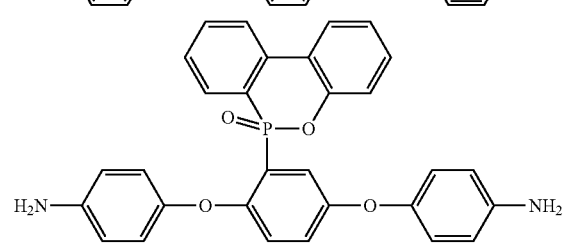
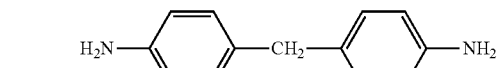
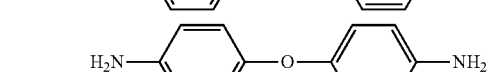
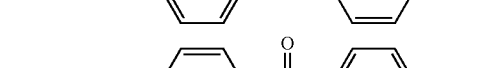
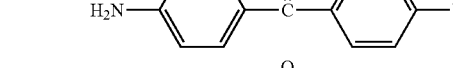
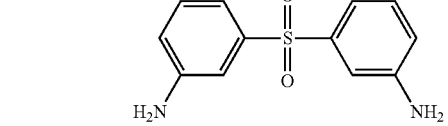
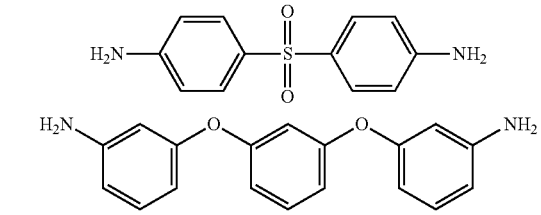
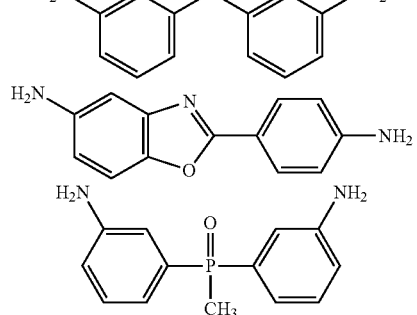
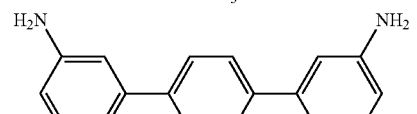
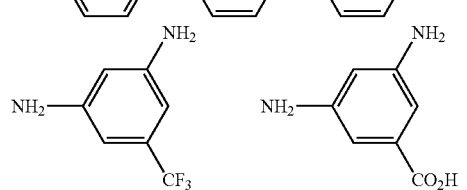
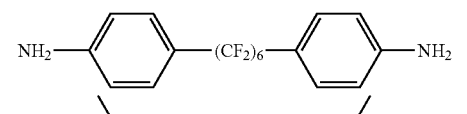
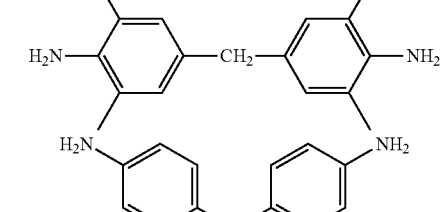
$X_1 = O, CH_2,$
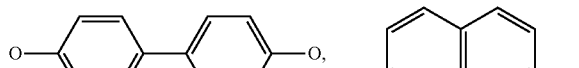
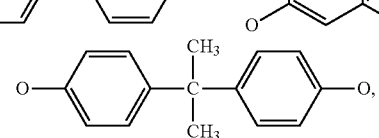
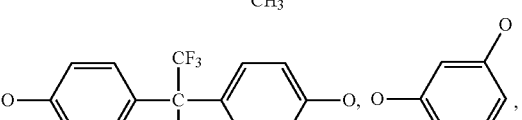
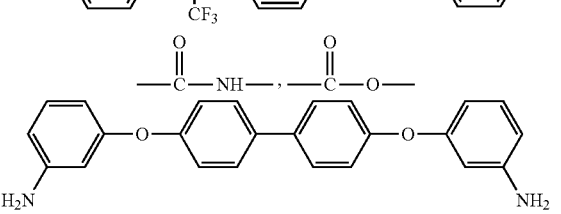

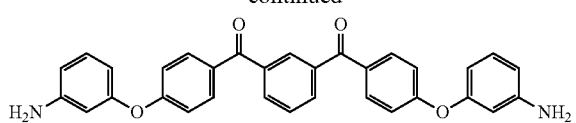
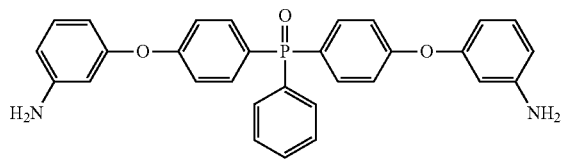
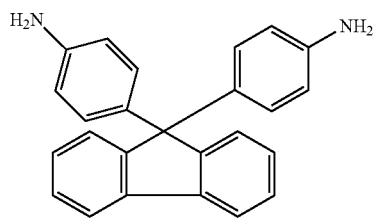
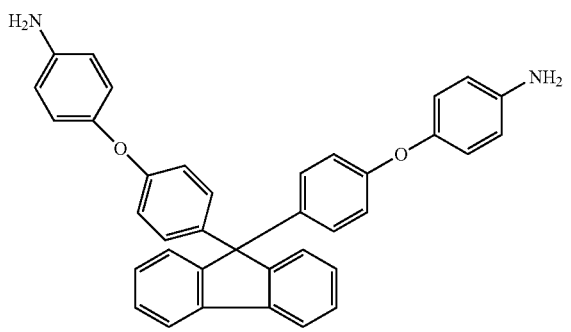
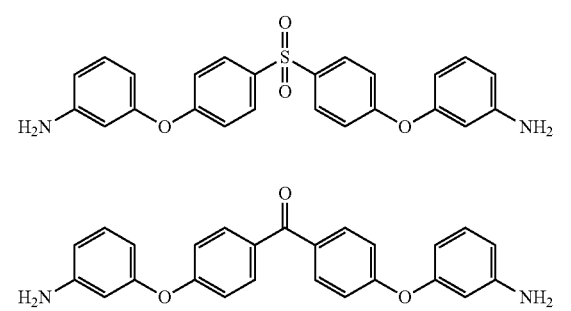
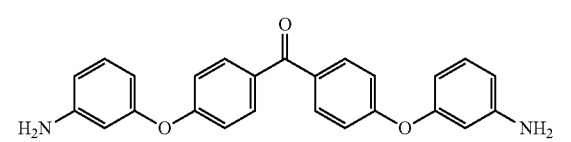

Examples of aromatic triamines include:

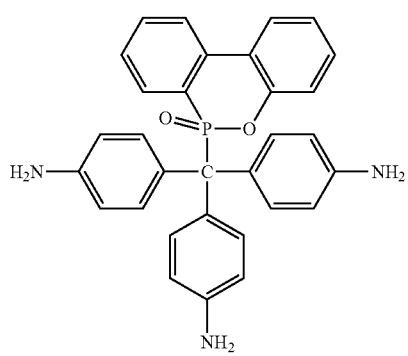
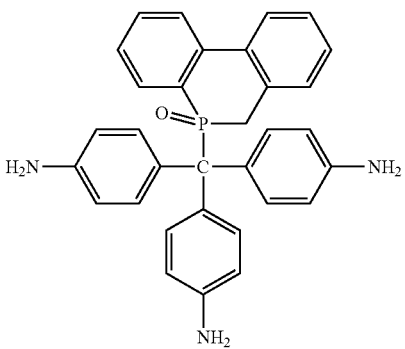

Phenols

In some embodiments, the phenol includes structures represented by the following Formulas IV, V and VI:

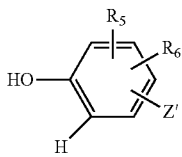

Formula IV

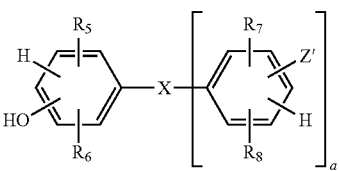

Formula V

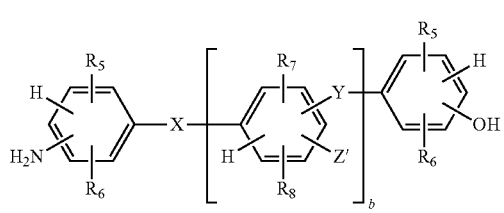

Formula VI wherein a=1 or 2; and b=0-50;

in Formula VI, X and Y are linking groups that are independently selected from a direct bond, O, S, $SO_2$, P=O, (Ph)P=O, OP(=O)O, C=O, substituted or unsubstituted alkylene, substituted or unsubstituted alkylidene, oxoalkylene, substituted or unsubstituted cycloaliphatic or aromatic group, where Ph is phenyl; Z' is H or OH; $R_5$, $R_6$, $R_7$ and $R_8$ are same and/or different and independently selected from hydrogen, halogen, substituted or unsubstituted alkyl, alkenyl, alkynyl or alkoxy of C1 to C20 carbon atoms, carboxyl, cyano, aryl, aralkyl or aryloxy group, and optionally when $R_5$ and $R_6$ and/or $R_7$ and $R_8$ taken together being a part of a saturated or unsaturated fused carbocyclic ring optionally containing O, N or S atoms in the ring, with the proviso that each phenolic OH has at least one ortho hydrogen in the aromatic ring;

in Formula V, when a=1, X is as defined for Formula VI, and when a=2, X is one of the following:
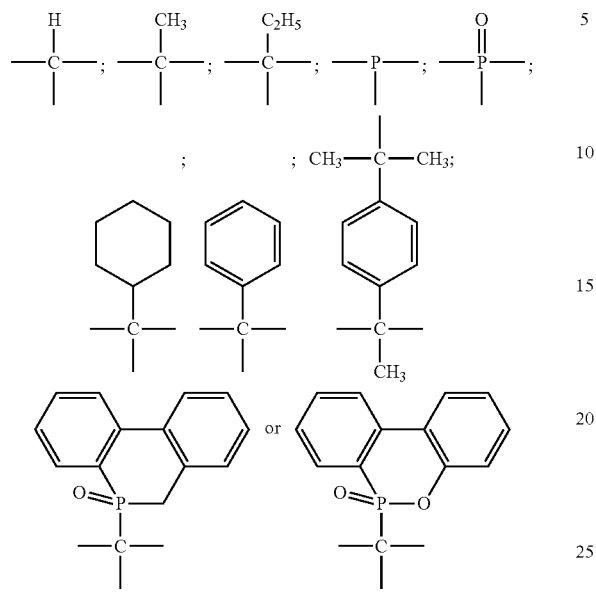
Thus, suitable phenols include monophenolic and polyphenolic compounds. Some specific examples of monophenolic compounds include:
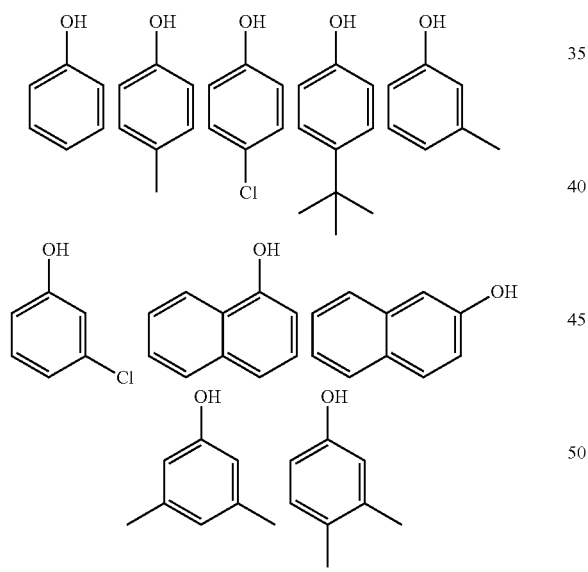
Examples of suitable bisphenolic compounds include:
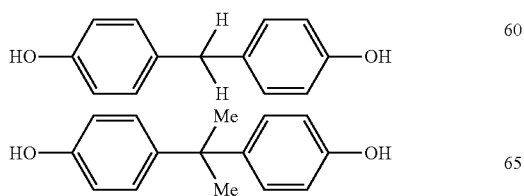
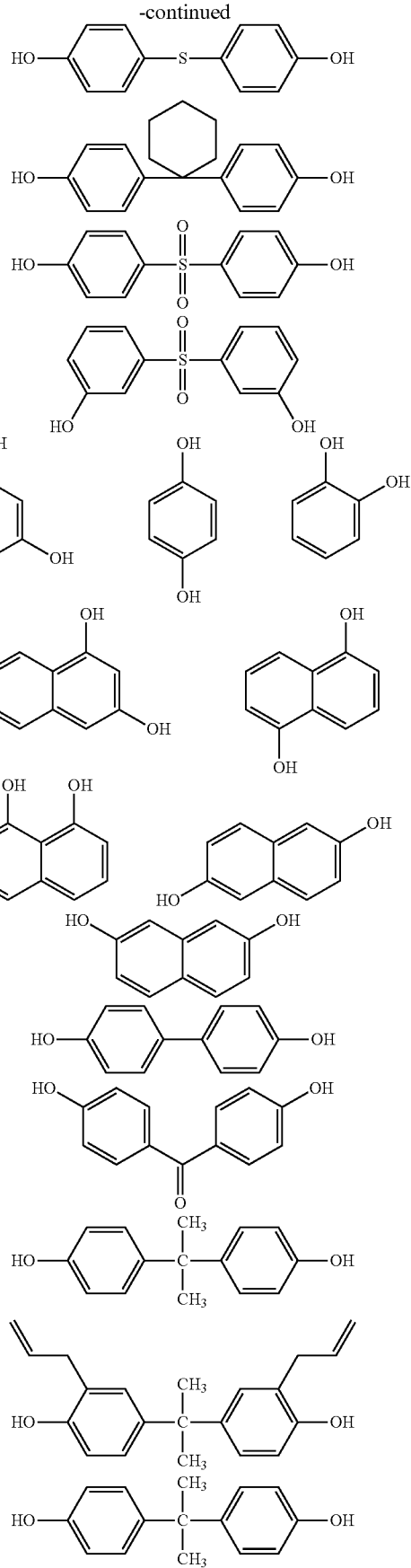

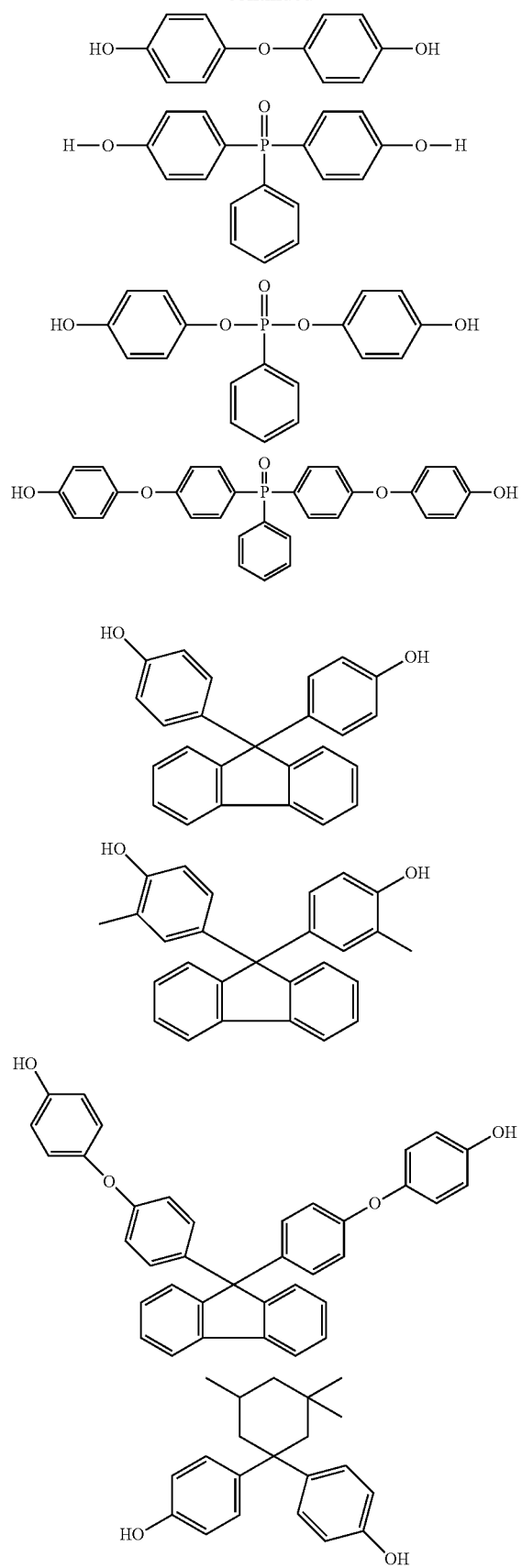
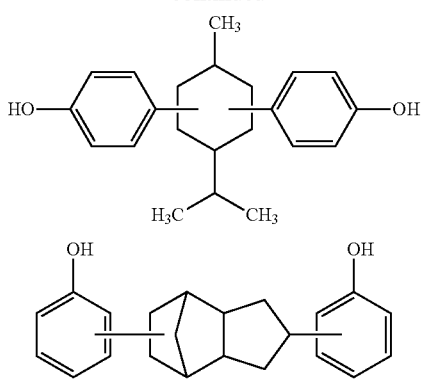
Examples of suitable trisphenolic compounds include:
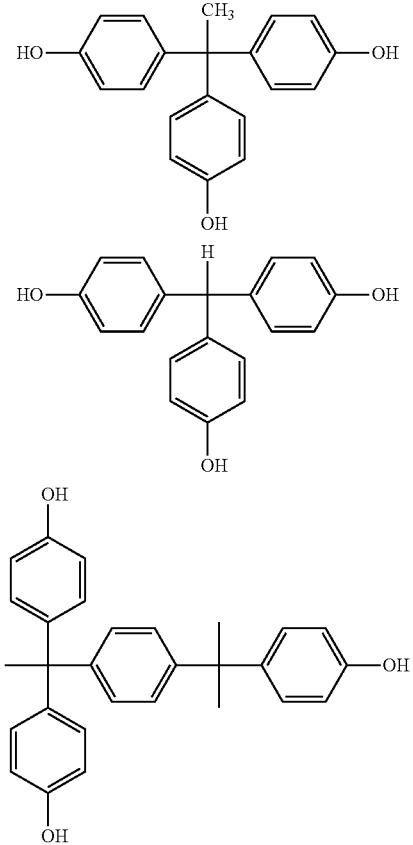
Also suitable are polyphenolic compounds represented by the following formulas:
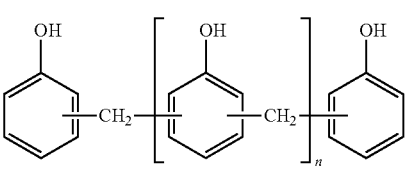

-continued

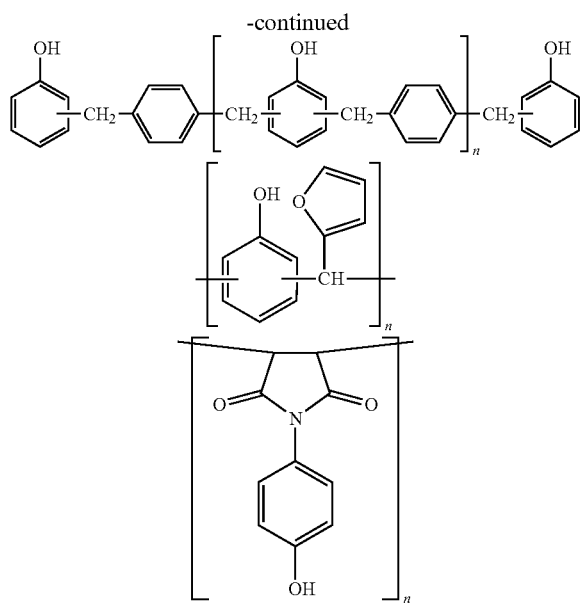

where n=1-50 for the above polyphenolic compounds.

Alkyl Formcel

The alkyl formcel is defined herein as a class of compounds comprising alkoxymethanol, $ROCH_2OH$. The R group in the alkyl formcel is selected from C1-C12 straight chain, branched chain, acyclic or cyclic, saturated or unsaturated hydrocarbyl group; preferably, R=C1-C4 alkyl group, and most preferably R=methyl. Specific examples of commercially available alkyl formcel include methyl formcel (methoxymethanol, CAS Reg #4461-52-3) and butyl formcel (butoxymethanol, CAS Reg #3085-35-6) (Celanese).

Alkoxymethyl Intermediate

The alkoxymethyl intermediate compound, which is the reaction product of aromatic amine and alkyl formcel, is represented by the following Formula VII:

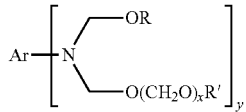

Formula VII where x=0-10 and y=1-10; in some embodiments, x=0-5 and y=1-5; in other embodiments, x=0-2 and y=1-3; R' is H or R; R is selected from C1-C12 straight chain, branched chain, acyclic or cyclic, saturated or unsaturated group; Ar is the aromatic residue part of the amine of Formulas I, II or III.

Stoichiometry

In the reaction to form benzoxazine discussed above, the stoichiometry of the reactants may be as follows: for each mole of aromatic amine ($NH_2$), there are about 1.5 to about 20 moles, or about 2 to about 20 moles, or about 2 to about 10 moles of alkyl formcel; and about 0.8 to about 1.25 mole of monohydric phenol or about 0.4 to about 0.625 mole of dihydric phenol (or bisphenol).

Process Conditions

In one embodiment, the phenol and the aromatic amine are mixed first at room temperature (20° C.-26° C.). Then alkyl formcel is added gradually to the mixture so that the exothermic reaction is well under control, preferably, the temperature is controlled to be in the range of 50° C.-60° C. without heating. Next, the resultant reaction mixture is refluxed at a refluxing temperature, which may vary depending on the solvent, while the reaction mixture is placed under inert atmosphere, e.g. nitrogen, for a period of time to complete the reaction while collecting the evaporated solvent. Suitable solvents include alcohols, dialkyl ketones, aliphatic hydrocarbons, aromatic hydrocarbons, dialkyl ethers, cyclic ethers, or combination thereof. Exemplary solvents include methanol, methyl ethyl ketone, methyl butyl ketone, methyl isobutyl ketone (MIBK), cyclohexanone, dioxane, tetrahydrofuran (THF), n-heptane, n-octane, toluene, and xylenes. After refluxing, the reaction product undergoes a work-up procedure, which includes: dissolving the reaction product in an organic solvent; diluting the resultant mixture in an aqueous solution containing an organic solvent and water; allowing the aqueous and organic layers to separate; washing with an aqueous solution containing an organic solvent and water. The organic solvents for the work-up process may include dichloromethane, 1,2-dichloroethane, methyl isobutyl ketone (MIBK), and ethyl acetate.

In an alternative embodiment, the process as described above is performed without collecting (i.e. removing) the evaporated solvent during refluxing.

In yet another embodiment, the alkyl formcel and the aromatic amine are mixed first at room temperature to form a pre-reacted product (i.e., until the disappearance of the aromatic amine is observed), forming the alkoxymethyl intermediate of Formula VII discussed above. The pre-reacted product has been analyzed to contain generally a mixture of components of general Formula VII. Then, the phenol is admixed with the pre-reacted product comprising the compound of Formula VII. The resultant reaction mixture is refluxed at a refluxing temperature while the mixture is placed under inert atmosphere, e.g. nitrogen, for a period of time to complete the reaction. The reaction product then undergoes a work-up process as described above to obtain the benzoxazine monomers. In some cases, the reaction product may contain minor amounts of other by-products or impurities.

In yet another embodiment, the N-alkoxymethyl intermediate formed from aromatic amine and alkyl formcel is isolated after it is formed. The isolated N-alkoxymethyl intermediate can be then be used at a later time as a reactant in the synthesis of benzoxazine or in an entirely different synthesis. For example, the N-alkoxymethyl intermediate may be used as a crosslinker for thermoset resins or coating application.

Microreactor Process

The reactions disclosed herein may be carried out using microreactor technology. The drawing FIGURE illustrates an exemplary microreactor system, which generally operates in a continuous flow mode. Pump A, a high pressure, high capacity syringe pump, is charged with solution A (e.g. the previously prepared alkyl formcel intermediate), and Pump B, a second similar syringe pump, is charged with solution B (e.g. phenol). These pumps are connected to a ternary static mixer, the outlet of which is connected to a stainless steel reaction coil (e.g. 1/16" OD×0.04" ID×10 meters tubing), and then to a backpressure regulator and a short outlet line. All connection tubing is of the same material as that used for the reaction coil. The tubing from the exit of the reaction coil to the end of the outlet line is heat-traced with a heating tape, insulated (e.g. with glass wool), and kept at a desired temperature using a temperature controller. The reaction coil is immersed in a heating medium (e.g. an oil bath) maintained at a temperature range suitable for affecting reaction.

In a typical reaction condition, flow rates are adjusted for Pumps A and B to give a desired molar ratio of reactants and residence time in the reaction coil. Samples are typically taken after allowing the system to equilibrate for two times the residence time, and the samples are then analyzed by High-Performance Liquid Chromatography (HPLC), High-Performance Size-Exclusion Chromatography (HPSEC), Liquid Chromatography-Mass Spectrometry (LCMS), and Nuclear Magnetic Resonance (NMR).

Applications of Benzoxazines

The benzoxazine compounds disclosed herein readily polymerize via ring opening polymerization. Such polymerization is usually initiated cationically (using cationic initiators) or thermally.

Moreover, the benzoxazine compounds of the present disclosure could be blended with other benzoxazine monomers or oligomers or other thermosettable resins to form polymer blends with desired properties. Other thermosettable resins that could be used in a blend with the benzoxazine compounds include: epoxy resins, bismaleimide (BMI), formaldehyde condensate resins such as formaldehyde-phenol resin, cyanate ester, unsaturated polyester, phenolic resins, and combinations thereof.

The benzoxazine blends discussed above may be combined with additional components such as catalysts and toughening agents to form a curable composition suitable for the manufacture of resinous films (e.g. adhesive films, surfacing films) or fiber-reinforced composites (e.g. prepregs).

Blends of benzoxazine monomers/oligomers and other thermosettable resins may be formulated so as to form curable resin compositions having properties that are suitable for composite fabrication using standard composite fabrication techniques such as prepregging and resin infusion.

EXAMPLES

In all Examples below, "equivalent" refers to molar ratio based on the moles of aromatic amine used.

HPLC is High Performance Liquid Chromatography.
LCMS is Liquid Chromatography Mass Spectrometry.
GCMS is Gas Chromatography Mass Spectrometry.
HPSEC is High Performance Size Exclusion Chromatography.
NMR is Nuclear Magnetic Resonance Spectroscopy.
DSC is Differential Scanning calorimetry.
TLC is Thin Layer Chromatography.

Example 1

Synthesis of Monofunctional Benzoxazines Using Paraformaldehyde (Conventional)

Monofunctional benzoxazines (Structures 1 and 2) were synthesized based on a conventional reaction represented below.

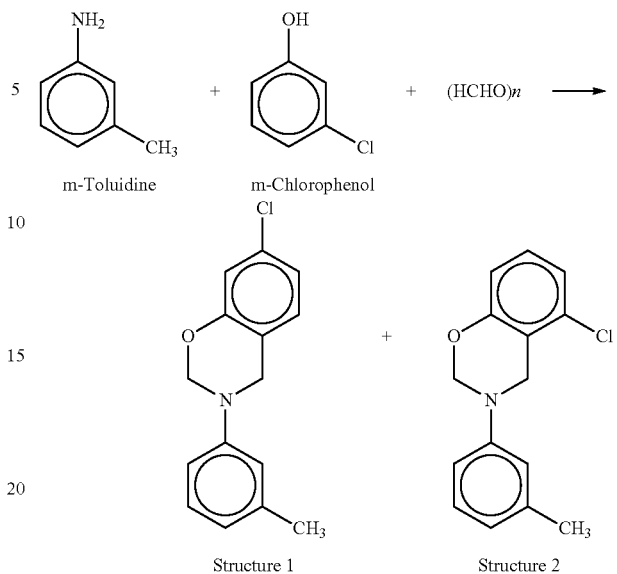

1 equivalent of m-toluidine, 1.05 equivalent of m-chlorophenol, and 3.5 equivalents of paraformaldehyde were added to a 4-neck round bottom flask equipped with an overhead stirrer, a thermocouple, a reflux condenser, a dropping funnel and a nitrogen inlet. An exotherm was observed at this stage. The reaction mixture was stirred and temperature was increased gradually. At approximately 65° C., a sudden exotherm (another exotherm) was observed and the temperature of the reaction went from 65° C. to 95° C. After 5 hours, no more peak due to starting materials was observed in HPLC. The heating was continued for an additional 1 hour, but no change in HPLC was observed. The heating was discontinued and the mixture underwent a standard work-up procedure which involved transferring the reaction mixture with toluene as diluent/solvent to a separation funnel and washing with 50 mL of 5% aqueous sodium hydroxide solution. However, an unbreakable emulsion was formed that resulted in discarding the reaction mixture. Thus, the conventional procedure resulted in sudden exotherm, and product isolation was difficulty due to the emulsion issue.

Example 2

Synthesis of Monofunctional Benzoxazines Using Paraformaldehyde and Isolation Procedure 50 g (1 equivalent) of m-toluidine, 66 g (1.05 equivalent) of m-chlorophenol and 55 g (3.5 equivalents) of paraformaldehyde were added to a 4-neck round bottom flask equipped with an overhead stirrer, a thermocouple, a reflux condenser, a dropping funnel and a nitrogen inlet. An exotherm was observed at this stage. The mixture was stirred and temperature was increased gradually. At approximately 65° C., a sudden exotherm was observed and the temperature of the reaction went from 65° C. to 95° C. After 5 hours, no more peak due to starting materials was observed in HPLC. The heating was continued for an additional 1 hour but no change in HPLC was observed. The heating was discontinued and the mixture underwent a work-up process by first dissolving in 100 mL dichloromethane and transferring to a separatory funnel, and then diluting with 50 mL methanol and 15 mL water. The contents were mixed and the layers were allowed to separate. The lower layer was washed twice with methanol/water (50 mL/15 mL) solution and then the solvent was removed under reduced pressure to give a mixture of two isomeric benzoxazines Structures 1 and 2 and some oligomers as brownish thick liquid, which were characterized by LCMS, NMR, and HPSEC. The new work-up procedure solved the isolation issue, but sudden exotherm during the reaction stage remained.

Example 3

Synthesis of Monofunctional Benzoxazines Using Methyl Formcel and Isolation Procedure Monofunctional benzoxazines Structures 1 and 2, as disclosed in Example 1, were prepared using methyl formcel according to an embodiment of the present disclosure.

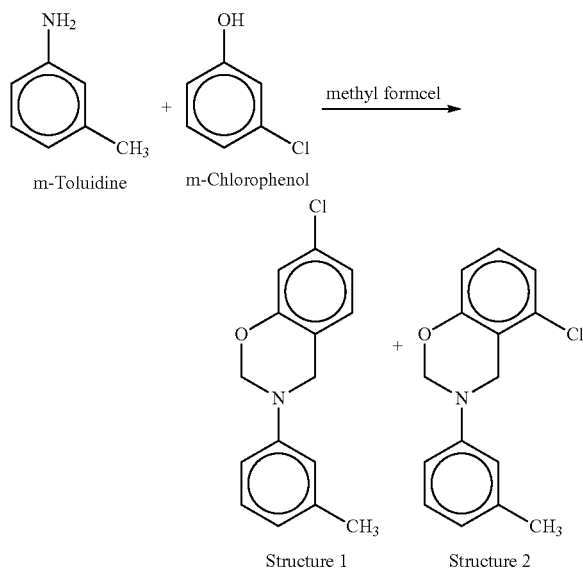

50 g (1 equivalent) of m-toluidine and 66 g (1.05 equivalent) of m-chlorophenol were added to a 4-neck round bottom flask equipped with an overhead stirrer, a thermocouple, a reflux condenser, a dropping funnel and a nitrogen inlet. The mixture was stirred at room temperature for 15 minutes. At this stage, 100 mL (3.5 equivalents) of methyl formcel (Methaform 55A, supplied by Momentive Specialty Chemicals, Inc., containing a solution of 55% formaldehyde, 10% water and 35% methanol with a pH of 5-6) was added gradually so that the exothermic reaction was well under control, and the temperature was allowed to rise to 55° C.-60° C. Once the addition of methyl formcel was complete, the reaction mixture was heated to reflux for 5 hrs. using an oil bath maintained at 110° C. while collecting methanol using a Dean-Stark apparatus. The heating was discontinued and the mixture underwent a work-up procedure by first dissolving the reaction mixture in 100 mL dichloromethane and transferring the mixture to a separatory funnel, and then diluting the separated product with 50 mL methanol and 15 mL water. The contents are mixed and the organic and aqueous layers are allowed to separate. The lower layer was washed twice with methanol/water (50 mL/15 mL) and then the solvent is removed under reduced pressure to give a mixture of two isomeric benzoxazines of Structures 1 and 2 and some oligomers as brownish thick liquid. This procedure solved the sudden exotherm problem associated with using paraformaldehyde and the isolation process worked well.

Example 4

Synthesis of Monofunctional Benzoxazines Using Methyl Formcel without Removal of Methanol During Reaction The reaction as described in Example 3 was repeated with a difference in that the Dean-Stark apparatus was not used and methanol was not removed during the course of the reaction. The work-up of the reaction product as described above yielded a product mixture containing benzoxazine monomers of Structures 1 and 2 with some oligomers. This product mixture was similar to that synthesized in Example 3.

Example 5

Synthesis of Monofunctional Benzoxazines by Pre-Reacting m-Toluidine with Methyl Formcel 90 mL (3 equivalent) of methyl formcel was added to a 4-neck round bottom flask equipped with an overhead stirrer, thermocouple, reflux condenser, dropping funnel and a nitrogen inlet. To this flask, 50 g (1.0 equivalent) of m-toluidine was added drop-wise at room temperature with effective control of the exotherm. The mixture was stirred at room temperature for approximately 120 minutes, resulting in the formation of a pre-reacted product ("pre-react") containing N-methoxymethyl intermediate. 66 g (1.05 equivalent) of m-chlorophenol was added drop-wise to the pre-reacted product with vigorous stirring. The addition rate was tuned to control the temperature of the reaction between 40° C.-50° C. without external heating. The reaction mixture was then heated to around 90° C. (using an oil bath maintained at 110° C.) and the progress of the reaction was monitored by HPLC for the disappearance of the starting materials and formation of the desired reaction product. After 3-4 hours, the heating was discontinued and the mixture underwent the work-up process described in Example 3 to yield an orange, highly viscous liquid, which was characterized by LCMS and HPSEC to contain benzoxazines of Structures 1 and 2 with some oligomers.

Example 6

Microreactor/Flow-Reactor Process for Making Benzoxazine

Preparation of Pre-React 3.5 equivalent of methyl formcel was added to a 4-neck round bottom flask equipped with an overhead stirrer, thermocouple, reflux condenser, dropping funnel and a nitrogen inlet. 1.0 equivalent of m-toluidine was added drop-wise to the flask at room temperature. The mixture was stirred at room temperature for approximately 120 minutes. At this stage, a pre-reacted product containing N-methoxymethyl intermediate was formed.

Feeding to the Pump

Two high pressure, high capacity syringe pumps (Pumps A and B) were connected to a ternary static mixer (as shown in FIG. 1). The outlet of the static mixer was connected to a stainless steel reaction coil (1/16" OD×0.04" ID×10 meters tubing), then to a stainless steel backpressure regulator and a short outlet line. All tubing was of the same stainless steel as the reaction coil. The tubing from the exit of the reaction coil to the end of the outlet line was heat-traced with a heating tape, insulated with glass wool and was kept at 45° C. using a temperature controller. The reaction coil was immersed into the oil of an oil bath filled with silicon fluid and initially at 75° C. Pump A was loaded with 294.84 g of the N-methoxymethyl intermediate and Pump B with 135.8 g of m-chlorophenol and each pump was cleared of its headspace air.

Table 1 provides the conditions for the microreactor process.

TABLE 1

| Phenol to Toluidine Molar Ratio | 1.05 | 1.05 | 1.05 | 1.05 | 1.05 | 1.05 | 1.05 |
|---|---|---|---|---|---|---|---|
| Total flow (µL/min) | 2,000 | 1,000 | 1,000 | 405 | 1,000 | 405 | 1,000 |
| Residence time in reaction coil (min) | 4.1 | 8.1 | 8.1 | 20.0 | 8.1 | 20.0 | 8.1 |
| Oil bath temperature (° C.) | 75.0 | 75 | 90 | 90 | 100 | 100 | 110 |
| Reactor Pressure (nominal, psig) | 40 | 40 | 40 | 40 | 40 | 40 | 40 |

Representative samples were collected upon achieving steady state under any particular set of conditions, and the samples were analyzed using HPLC, LCMS, SEC and NMR after the standard work-up process described in Example 3. The analysis confirmed the formation of the benzoxazines of Structures 1 and 2 and some oligomers.

Example 7

Comparative Results from Batch Reactor Process and Microreactor/Flow Reactor Process Benzoxazine samples were prepared according to the synthesis method described in Example 5 (samples #1 and 2) and using the micro-reactor process as described in Example 6 (samples #3-8). The following Table 2 summarizes the results based on HPSEC and LCMS analysis. The results demonstrated that the micro-reactor can be effectively used to make benzoxazines with the advantage of shorter time and more throughput.

TABLE 2

| | | | | | HPSEC Area % | | | | |
|---|---|---|---|---|---|---|---|---|---|
| Sample No. | Identity | Reaction Temp. | Batch/ Residence Time | Oligomer | Cl-Benzoxazine Isomers | | Isomer Ratio | | LCMS Amine Adduct Area % |
| | | | | | Major (1) | Minor (2) | Major (1) | Minor (2) | |
| 1 | Batch reactor | 90° C. | 30 min. | 24 | 57 | 19 | 75 | 25 | 5 |
| 2 | Batch | 90° C. | 60 min. | 29 | 52 | 19 | 73 | 27 | 2 |

TABLE 2-continued

| | | | | | Cl-Benzoxazine Isomers | | Isomer Ratio | | LCMS Amine |
|---|---|---|---|---|---|---|---|---|---|
| Sample No. | Identity | Reaction Temp. | Batch/ Residence Time | Oligomer | Major (1) | Minor (2) | Major (1) | Minor (2) | Adduct Area % |
| 3 | Micro reactor | 75° C. | 8 min. | 24 | 50 | 27 | 67 | 33 | 18 |
| 4 | Micro reactor | 90° C. | 8 min. | 10 | 51 | 39 | 57 | 44 | 21 |
| 5 | Micro reactor | 90° C. | 20 min. | 22 | 57 | 21 | 73 | 27 | 7 |
| 6 | Micro reactor | 100° C. | 8 min. | 10 | 50 | 40 | 56 | 44 | 16 |
| 7 | Micro reactor | 100° C. | 20 min. | 17 | 55 | 28 | 66 | 34 | 6 |
| 8 | Micro reactor | 110° C. | 8 min. | 19 | 55 | 26 | 68 | 32 | 15 |

Example 8

Synthesis of Monofunctional Benzoxazine Using Methyl Formcel

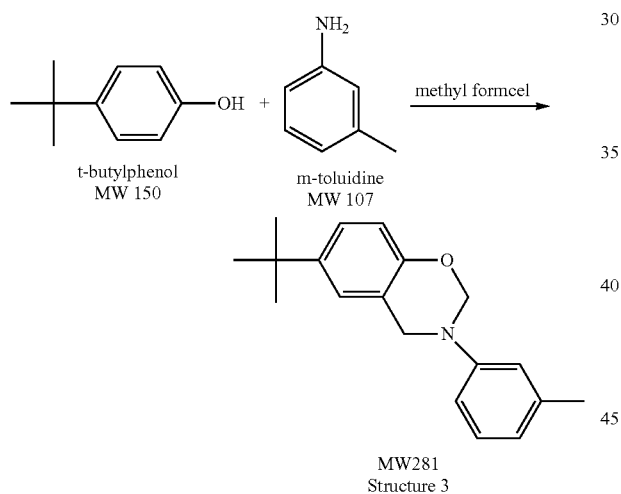

45 g (~3 equivalent) of methyl formcel was added to a 4-neck round bottom flask equipped with an overhead stirrer, thermocouple, reflux condenser, dropping funnel and a nitrogen inlet. 27 g (0.25M) of m-toluidine was added drop-wise to the flask at room temperature. The mixture was stirred at room temperature for approximately 120-180 minutes (or until consumption of m-toluidine and formation of a pre-reacted product were observed). 42 g (0.27 M) of t-butylphenol was added portion-wise over 15 minutes with vigorous stirring. No exothermic was observed and the reaction temperature during the addition of t-butylphenol was around 20° C. The reaction mixture was then heated to around 90° C. (using an oil bath maintained at 110° C.) and the progress of the reaction was monitored by TLC and HPLC for the disappearance of the starting materials and formation of the desired product. After 6 hours, the heating was discontinued and the mixture underwent a standard work-up procedure, i.e., the reaction mixture was transferred to a separatory funnel with 100 mL dichloromethane and 50 mL methanol, and to this solution, 15 mL of water was added followed by removal of top layer; bottom layer was washed with methanol/water mixture (50 mL/15 mL) three times; the organic bottom layer was then washed with brine solution, dried using $MgSO_4$, filtered; dichloromethane was removed under reduced pressure to yield an orange, highly viscous liquid, which was characterized based on NMR and LCMS to be the benzoxazine compound of Structure 3. The weight of the final product formed was 57 gm (% yield=81%).

Example 9

Synthesis of Di-Functional Benzoxazine Using Methyl Formcel

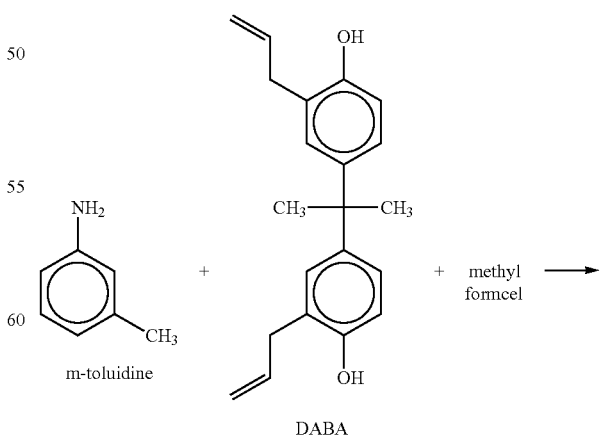

-continued

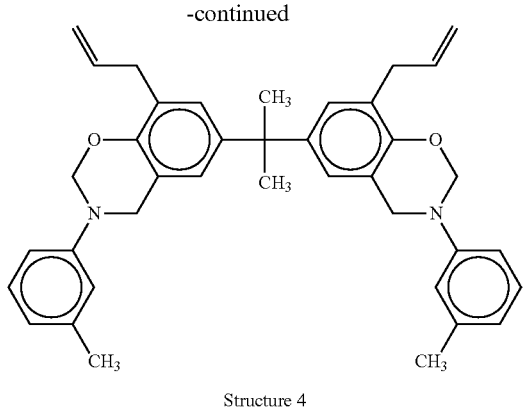

Structure 4

325 g (2 equivalent) of m-toluidine and 450 g (1.05 equivalent) of DABA (diallyl-bisphenol-A) to a 4-neck round bottom flask equipped with an overhead stirrer, a thermocouple, a reflux condenser, a dropping funnel and a nitrogen inlet. The mixture was stirred at room temperature for approximately 15 minutes. Next, 450 mL (5.5 equivalent) of methyl formcel was added drop-wise with vigorous stirring. The reaction was exothermic, but the addition rate was tuned to control the temperature of the reaction between 50° C.-60° C. without external heating. The reaction mixture was then heated to around 85° C.-100° C. (using oil bath maintained at 110° C.) and the progress of the reaction was monitored by HPLC for the disappearance of the starting materials and formation of the desired product. After 5 hours (once no more peak due to m-toluidine was observed and almost all methanol was distilled out), the heating was discontinued and the mixture underwent the standard work-up procedure. The reaction mixture was transferred to a separatory funnel with 1 L dichloromethane, and washed with 250 mL methanol and 75 mL of water, followed by removal of top layer. Bottom layer containing the product was washed twice with methanol/water mixture (250 mL/75 mL). The organic layer was then washed with a brine solution, dried, filtered, and dichloromethane was removed under reduced pressure to yield a pale yellow, highly viscous liquid that was characterized by LCMS to contain di-functional benzoxazine of Structure 4 as the only major component.

Example 10

Synthesis of Di-Functional Benzoxazine Using Methyl Formcel

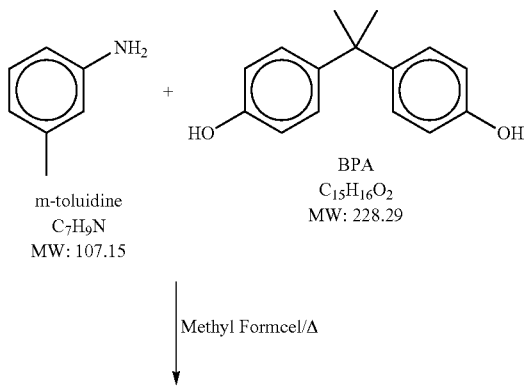

-continued

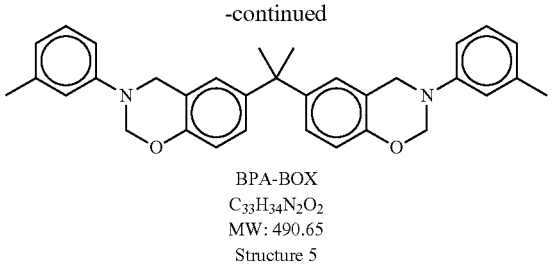

BPA-BOX
C$_{33}$H$_{34}$N$_2$O$_2$
MW: 490.65
Structure 5

360 mL (6.0 mol) of methyl formcel was charged to a 4-neck 3 L round bottom flask equipped with a reflux condenser, a Dean-Stark trap, overhead stirrer, a thermocouple, a dropping funnel and a N$_2$ inlet. Then 216 g (2.0 mol) of m-toluidine was added drop-wise with stirring through the dropping funnel. An exothermic reaction was observed but the rate of m-toluidine addition was controlled to keep the temperature of the reaction mixture below 40° C. After the m-toluidine addition, the reaction mixture was stirred for 2 hours at 40° C. Next, 230 g (1.0 mol) of bisphenol-A (BPA) was added in 15 g portions over 40 minutes at 40° C. with stirring. After the BPA addition, the reaction was stirred at 80-85° C. for 6 hours. The heating was turned off and the the reaction mixture was allowed to cool down to 50° C.

Subsequently, the reaction mixture underwent a standard work-up procedure. 900 mL of methylene chloride was added to the reaction mixture and stirred for 20 minutes. Then, 220 mL of water and 215 mL of methanol were added and stirred for 15 minutes. The reaction mixture was transferred to a 2 L separatory funnel, and the aqueous and organic layers were allowed to separate. The bottom organic layer, which contained the reaction product, was separated by removing the aqueous layer. The organic layer was washed twice with methanol/water mixture (220 mL/215 mL). The solvent was removed under vacuum to obtain 400 g-430 g (82-88% yield) of the m-bis-BPA-Benzoxazine Structure 5 as an amber color liquid. The benzoxazine compound was analyzed by LC-MS to have a MW of 490.65 g/mol.

Example 11

Synthesis of Tri Functional Benzoxazine Using Methyl Formcel

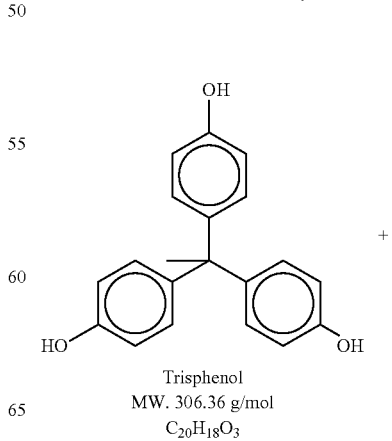

Trisphenol
MW. 306.36 g/mol
C$_{20}$H$_{18}$O$_3$

-continued

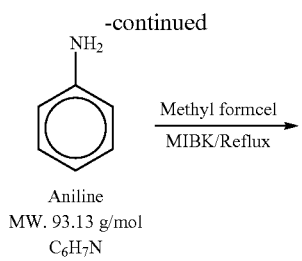

Aniline
MW. 93.13 g/mol
C₆H₇N

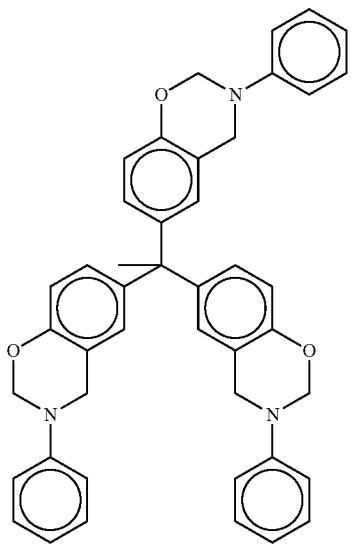

Aniline Tris BOX
MW. 657.81 g/mol
C₄₄H₄₉N₃O₃
Structure 6

In a 4 neck 1 L round bottom flask equipped with an overhead stirrer, thermocouple, reflux condenser, Dean-Stark trap, dropping funnel and a N₂ inlet, 324 mL (9.00 equivalents) of methyl formcel was combined with 100 mL of MIBK (methyl isobutyl ketone). To this mixture, 186 mL (3.00 equivalent) of aniline was added drop-wise. The reaction mixture was stirred at ambient temperature for 3 hrs, and then 200 g (1.02 equivalent) of tris-phenol was added in bulk through a powder funnel. The reaction was refluxed for 9.5 hours and about 130 mL of condensate was removed via Dean-Stark trap. The heating was turned off and the reaction product was allowed to cool down to ambient temperature.

Subsequently, the reaction product underwent a standard work-up procedure. 200 mL of dichloromethane was added to the reaction and stirred for one hour. Next, the resulting mixture was transferred to a 2 L separatory funnel. 100 mL of methanol was added to the mixture in a separatory funnel and shaken vigorously. 30 mL of deionized (DI) water was added to the separatory funnel to aid the breakup of the emulsion formed during the vigorous shaking. The top aqueous layer was removed and discarded while the bottom layer was returned back to separatory funnel. This methanol/water treatment step. This step was repeated three (3) more times, followed by consecutive extractions with 100 mL water and of 200 mL of brine solution. The organic layer was dried over anhydrous magnesium sulfate, and the solvent was removed under vacuum to yield a reaction product in the form of a viscous liquid.

Subsequently, a work-up procedure was carried out. The resulting viscous liquid was re-dissolved using 100 mL of dichloromethane. This solution was poured into 500 mL of methanol in 1 L beaker and stirred with an overhead stirrer to obtain a white paste like precipitate. The solvent was decanted, and more methanol was added and further stirred. Again, the solvent was decanted. This methanol treatment was repeated once more and the material was dried in a vacuum oven at ambient temperature to remove any remaining methylene chloride/methanol to obtain 379.8 g (90% yield) of a reaction product in the form of a solid. The reaction product was characterized by TLC, LC-MS and NMR to be mainly the tri-functional benzoxazine of Structure 6 with MW of 657.81 g/mol.

Example 12

Synthesis of Tri-Functional Benzoxazine Using Methyl Formcel

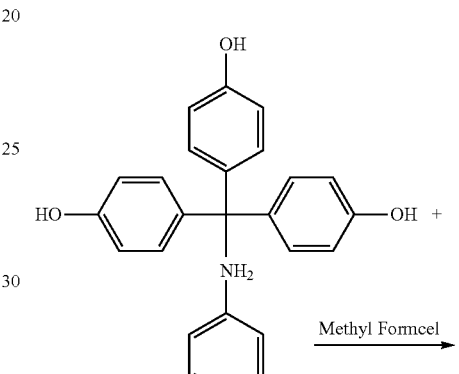

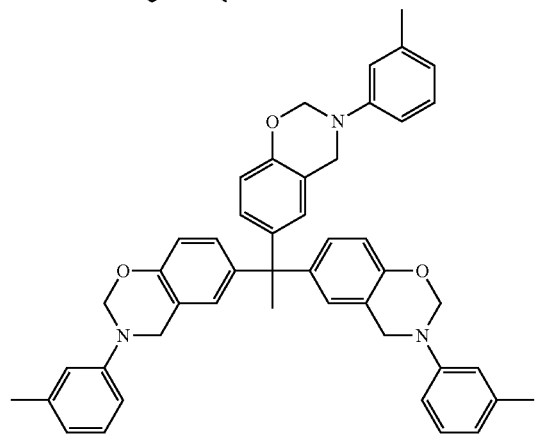

Tris-BOX with m-toluidine
Structure 7

81 mL of methyl formcel (1.48 mole) was added to a 4-neck round bottom flask equipped with reflux condenser, thermocouple, overhead stirrer and a nitrogen inlet. To the flask, 54 g (0.5 mole) of m-toluidine was added drop-wise. The solution was then stirred for 2 hrs. at room temperature. The disappearance of m-toluidine was observed by TLC. At this stage, solid 1,1,1-tris (4-hydroxyphenyl) ethane was added in portions. The reaction mixture was then heated to reflux. The reaction was monitored by HPLC which showed one major product peak. The reaction mixture was cooled and then underwent the work-up procedure as discussed in the above Example 11 by diluting the reaction mixture with methylene chloride. The resulting solution was then washed with methanol/water mixture. The methylene chloride layer (which contained reaction product) was dried with Na$_2$SO$_4$, filtered, and the solvent removed under reduced pressure. The residue was treated with methanol to obtain a white solid, which was filtered, washed with methanol and dried. The resulting solid was characterized by LCMS and by NMR spectroscopy, showing the tri-functional benzoxazine of Structure 7 as the major component with MW of 699 g/mol.

Example 13

Preparation of 4,4'-DDS Based Bisbenzoxazine from Methyl Formcel and t-Butylphenol

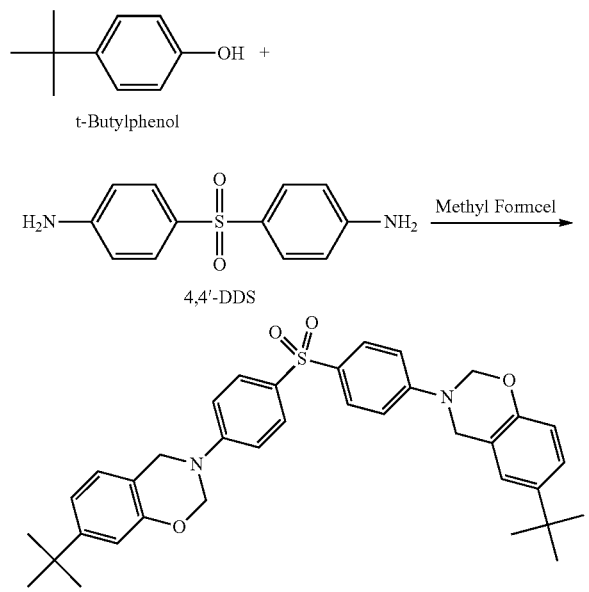

45 g (0.8 M) of methyl formcel was added to a 4-neck round bottom flask equipped with an overhead stirrer, thermocouple, reflux condenser, dropping funnel and a nitrogen inlet. To this flask, at room temperature, 4,4'-DDS (31 g; 0.12 M) was added in portions over 15 minutes. The mixture was stirred at room temperature for approximately 120-180 minutes (until consumption of 4,4'-DDS was observed). The mixture was heated to 50° C. and stirred for 4 hrs. T-butylphenol (42 g; 0.27 M) was added portion-wise over 15 minutes with vigorous stirring. No exotherm was observed. The reaction mixture was then heated to around 90° C. (oil bath temperature 110° C.) and the progress of the reaction was monitored by TLC. After 8 hours, the heating was discontinued and the mixture was worked up as follows.

Work-Up Procedure 150 ml of methanol was added to the reaction mixture which led to precipitation of the product. The product was filtered and dried under reduced pressure. NMR and HPLC analysis of the sample was carried out. The weight of the filtered product was 31 g (% yield=55%). The mother liquor also contained some of the product.

Example 14

Reaction of 4,4'-DDS with Methyl Formcel and Isolation of the N-Methoxymethyl Intermediate

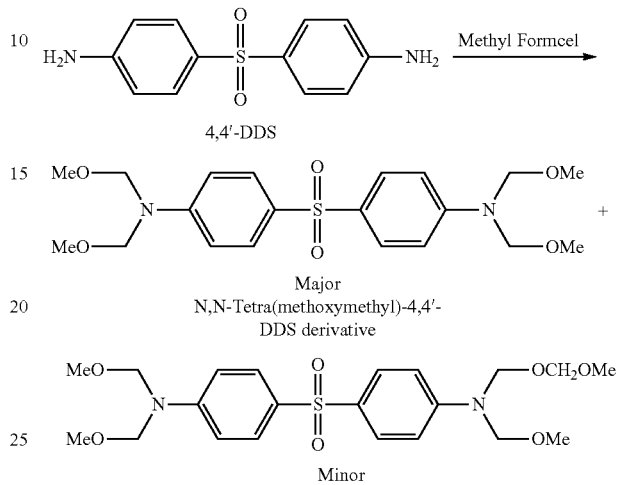

60 g of methyl formcel was added to a 500 mL 4-neck round bottom flask equipped with an overhead stirrer, thermocouple, reflux condenser, dropping funnel and a nitrogen inlet. The content was heated to 50° C. with stirring. To this flask, 30 g of 4,4'-DDS was added in portions over 15 minutes. About 80 mL methanol was added during the course of 4,4'-DDS addition. The temperature was increased to 60° C. and held for 2 hours. The mixture was then heated to reflux for 4 hours. It was then allowed to cool and the precipitate formed was filtered, washed with methanol, and dried to give 31.6 g of a product, which was characterized by LCMS to consist mainly of N,N'-tetra(methoxymethyl)-4,4'-DDS derivative. The filtrate was concentrated to give another 19.6 g of the product characterized by LCMS to be consisting mainly of N,N'-tetra(methoxymethyl)-4,4'-DDS and a minor component containing an additional CH$_2$ unit in one of the methoxymethyl group.

Example 15

Preparation of APB-133-Based Bis-Benzoxazine from Methyl Formcel and t-Butylphenol

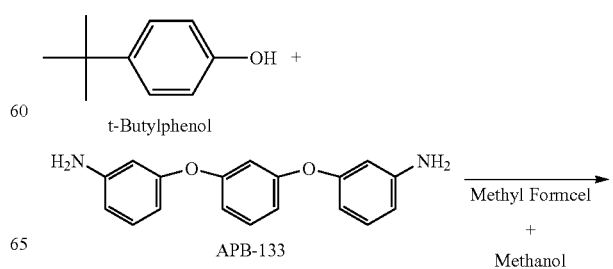

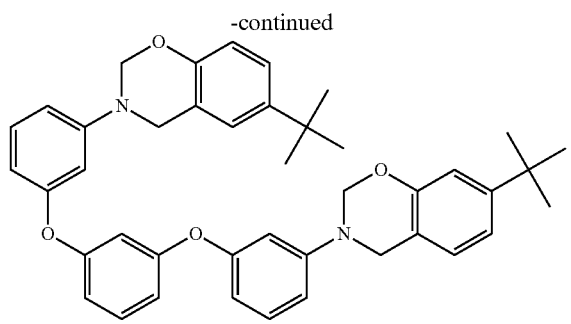

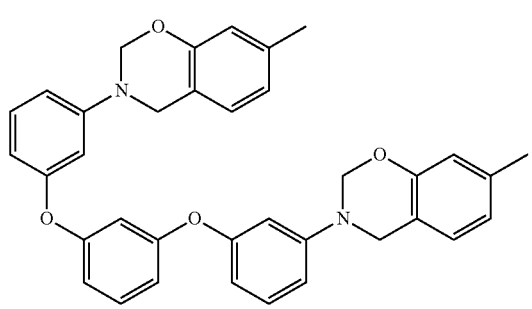

60 g of methyl formcel was added to a 4-neck round bottom flask equipped with an overhead stirrer, thermocouple, reflux condenser, dropping funnel and a nitrogen inlet. To this flask, at room temperature, 0.125 M of APB-133 [1,3'-Bis (3-aminophenoxy) benzene] (36.5 g) was added in portions. As viscosity of the mixture increases at this stage, 150 ml of methanol was added. The mixture was stirred at room temperature for approximately 120-180 minutes (until consumption of APB was observed via TLC). 42 g t-butylphenol (0.27 M) was added portion-wise over 15 minutes with vigorous stirring. No exotherm was observed. An additional 100 ml of methanol was added. The reaction mixture was then heated to around 90° C. (oil bath temperature 110° C.) and the progress of the reaction was monitored by TLC. 100 ml of methanol was then removed from the reaction mixture using Dean-Stark apparatus. After 6 hours, the heating was discontinued and the mixture was worked up using the standard procedure.

Work-Up Procedure

The reaction mixture was taken in separatory funnel with 300 mL dichloromethane and 100 mL methanol. To this solution, 100 mL of water was added followed by removal of the top layer. The bottom layer was treated with methanol water mixture three times. The organic layer was then washed with a brine solution, dried using MgSO$_4$, and filtered. Dichloromethane was removed under reduced pressure to yield an orange, highly viscous liquid. The weight of the product formed was 65 g (% yield=81%), which was characterized by LCMS to be the desired bis-benzoxazine based on APB-133.

Example 16

Preparation of APB-133-Based Bis-Benzoxazine from Methyl Formcel and m-Cresol 120 g (~8 equivalents) of methyl formcel was added to a 4-neck round bottom flask equipped with an overhead stirrer, thermocouple, reflux condenser, dropping funnel, and a nitrogen inlet. Methyl formcel was preheated to 50° C. before adding 73 g (0.25 M) of APB-133 in portions. The mixture was stirred at 50° C. for approximately 120 minutes (until consumption of APB was observed via TLC). 58.4 g of m-cresol (0.54 M) was added dropwise over 15 minutes with vigorous stirring. The reaction mixture was then heated to around 90° C. (oil bath temperature 110° C.) and the progress of the reaction was monitored by TLC. After 6 hours, the heating was discontinued and the mixture was worked up using standard procedure.

Work-Up Procedure

The reaction mixture was taken in a separatory funnel with 300 mL dichloromethane and 100 mL methanol, to this solution 100 mL of water was added followed by the removal of the top layer. The bottom layer was treated with methanol water mixture three times. The organic layer was then washed with a brine solution and dried under vacuum. The weight of the product formed was 160 g.

Example 17

Synthesis of Methylenediamine (MDA)-Based Bis-Benzoxazine Using Methyl Formcel and t-Butylphenol

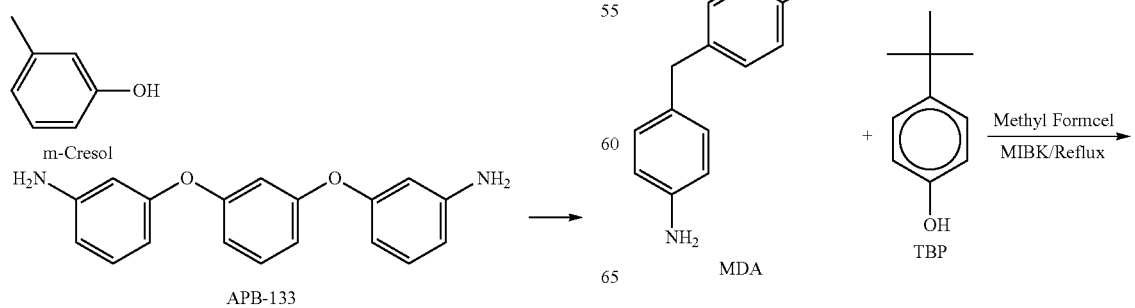

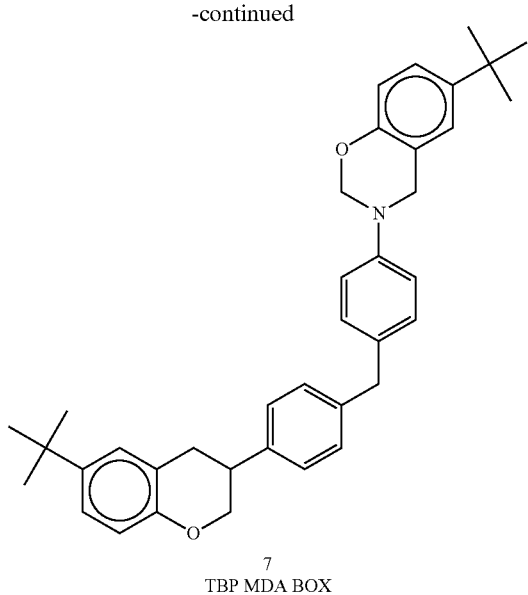

7
TBP MDA BOX 160 mL (8.0 equivalents) of methyl formcel was added to a 4 neck 1 L round bottom flask equipped with an overhead stirrer, reflux condenser, Dean-Stark trap, thermocouple and $N_2$ inlet, and heated up to 50° C. To this solution, 74.8 g (1.0 equivalent) of 4,4'-methylenedianiline (MDA) is added in 8.0 g portions via a powder funnel under constant stirring. 50 mL of MIBK was added as a co-solvent. The reaction was heated at 50° C. for 10 hours until the MDA spot on TLC has disappeared. A sample was taken and analyzed by LCMS. LCMS confirmed the formation of N-methoxymethyl intermediate. Then, 119.1 g (2.1 equivalents) of t-butylphenol (TBP) was added to the reaction in lots and refluxed for 6 hour while continuously removing methanol/water/MIBK mixture via Dean-Stark trap. The product formation was monitored by TLC and confirmed by LCMS. The product was isolated to yield 198 g (99% yield) by precipitating in methanol.

Example 18

Synthesis of Mono-Functional Benzoxazine Using Methyl Formcel

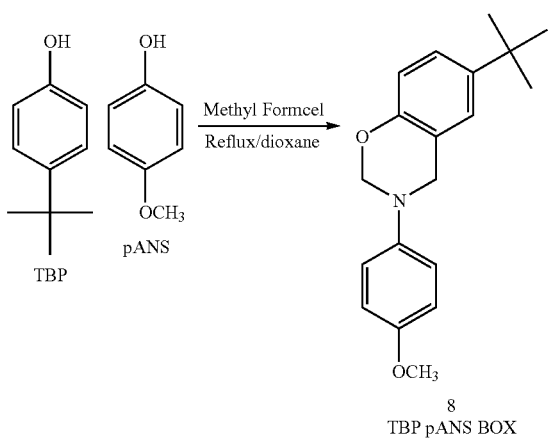

89.0 mL (4.0 equivalents) of methyl formcel was added to a 4-neck 500 mL round bottom flask equipped with an overhead stirrer, thermocouple, reflux condenser, Dean-Stark trap and a $N_2$ inlet, at room temperature. To this flask, 50.0 g (1.0 equivalent) of para-anisidine was added in approximately 10 g portions over 10-15 minutes. An exotherm (19° C.→37° C.) was observed upon para-anisidine addition and the color of the reaction mixture turned olive green. The reaction was heated to 50° C. for 5 hours. At this point, a sample was taken and analyzed by LCMS. The LCMS confirmed the formation of N-methoxymethyl intermediate. To this mixture, 61.0 g (1.0 equivalent) of tert-butylphenol (TBP) was added in lots. The reaction turned wine color upon TBP addition and then a white precipitate started to form. The reaction was refluxed for 3 hours; about 35 mL of MeOH/water was removed by Dean-Stark trap. 100 mL of MIBK was added to the reaction and refluxed for 3 hours. The completion of the reaction was monitored by TLC. Reaction was allowed to cool to room temperature. About 100 mL of MeOH was added to obtain the product as a white precipitate. It was filtered and washed with cold methanol for 3-4 times and dried under vacuum. The product structure was confirmed by NMR and LCMS.

Example 19

Synthesis of Bis-Benzoxazine Using Methyl Formcel

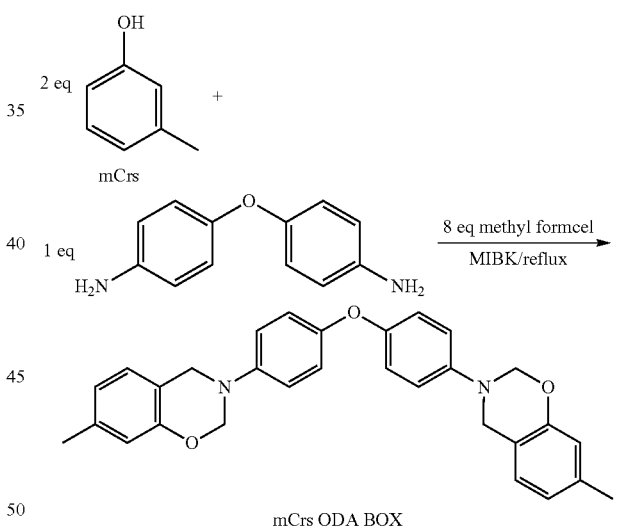

114 mL of methyl formcel was added to a 4-neck 1 L round bottom flask equipped with an overhead stirrer, thermocouple, reflux condenser, Dean-Stark trap, and a $N_2$ inlet, at room temperature. To this flask, 52.1 g (1.0 equivalent) of 4,4'-oxydianiline (ODA) was added in approximately 10 g portions over 10-15 minutes. The reaction was heated to 50° C. for 5 hours. At this point, a sample was taken and analyzed by LCMS. The LCMS data confirmed the formation of N-methoxymethyl intermediate. Into this mixture, 56.3 g (2.0 equivalents) of m-cresol was added via a dropping funnel. The reaction mixture was heated to reflux. Removal of 10 mL of MeOH/water distillate via Dean-Stark apparatus led to the formation of white solid. 200 mL of MIBK was added to the reaction mixture and refluxed for total of 6 hours while removing more distillate using Dean- Stark trap. The completion of the reaction was monitored by TLC. The reaction mixture was allowed to cool to room temperature. Addition of about 100 mL of MeOH yielded white precipitate, which was filtered and washed with cold methanol for 3-4 times and dried under vacuum. The structure of the bis-benzoxazine product was confirmed by NMR and LCMS.

Example 20

Synthesis of Methylenediamine (MDA)-Based Bis-Benzoxazine Using Methyl Formcel and t-Butylphenol

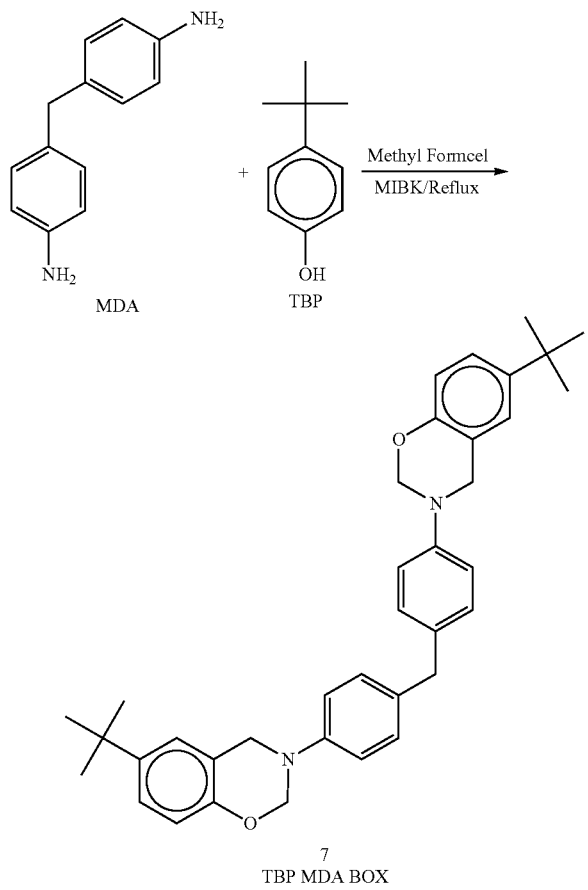

7
TBP MDA BOX 160 mL (8.0 equivalents) of methyl formcel was added to a 4 neck 1 L round bottom flask equipped with an overhead stirrer, reflux condenser, Dean-Stark trap, thermocouple and $N_2$ inlet, and heated up to 50° C. To this solution, 74.8 g (1.0 equivalent) of 4,4'-methylenedianiline (MDA) was added in 8.0 g portions via a powder funnel under constant stirring. 50 mL of MIBK was added as a co-solvent. The reaction mixture was heated at 50° C. for 10 hours until the MDA spot on TLC has disappeared. A sample was taken and analyzed by LCMS. LCMS confirmed the formation of N-methoxymethyl intermediate. Then, 119.1 g (2.1 equivalents) of t-butylphenol (TBP) was added to the reaction mixture in lots and refluxed for 6 hours while continuously removing methanol/water/MIBK mixture via Dean-Stark trap. The product formation was monitored by TLC and confirmed by LCMS. The product was isolated to yield 198 g (99% yield) by precipitating in methanol.

Ranges disclosed herein are inclusive and independently combinable, and is inclusive of the endpoints and all intermediate values within the ranges. For example, the range of "1% to 10%" includes 1%, 2%, 3%, 4%, 5%, 6%, 7%, 8%, 9%, 10% as well as intermediate values such as 1.1%, 1.2%, 1.3%, etc.

While various embodiments are described herein, it will be appreciated from the specification that various combinations of elements, variations of embodiments disclosed herein may be made by those skilled in the art, and are within the scope of the present disclosure. In addition, many modifications may be made to adapt a particular situation or material to the teachings of the embodiments disclosed herein without departing from essential scope thereof. Therefore, it is intended that the claimed invention not be limited to the particular embodiments disclosed herein, but that the claimed invention will include all embodiments falling within the scope of the appended claims.

What is claimed is:

1. A synthesis process comprising reacting an aromatic amine with an alkyl formcel for a sufficient time for the consumption of the aromatic amine so as to form an alkoxymethyl intermediate compound or a mixture of alkoxymethyl intermediate compounds, wherein the aromatic amine is selected from structures represented by Formulas I, II and III:

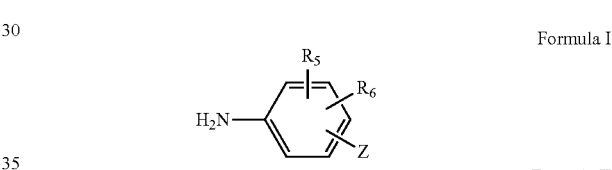

Formula I

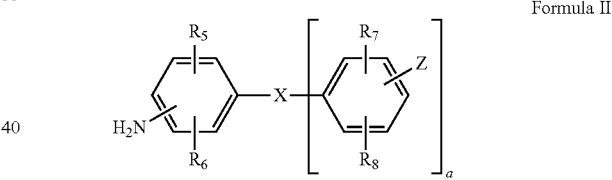

Formula II

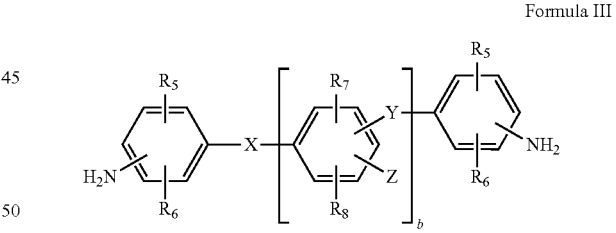

Formula III wherein a=1 or 2; and b=0-50;
in Formula III, X and Y are linking groups that are independently selected from a direct bond, O, S, SO2, P=O, (Ph)P=O, OP(=O)O, C=O, substituted or unsubstituted alkylene, substituted or unsubstituted alkylidene, oxoalkylene, substituted or unsubstituted cycloaliphatic or aromatic group, where Ph is phenyl; Z is H or $NH_2$; $R_5$, $R_6$, $R_7$ and $R_8$ are same or different and are independently selected from hydrogen, halogen, substituted or unsubstituted alkyl, alkenyl, alkynyl or alkoxy of C1 to C20 carbon atoms, carboxyl, cyano, aryl, aralkyl or aryloxy group, and optionally, $R_5$ and $R_6$ taken together and/or $R_7$ and $R_8$ taken together being a part of a saturated or unsaturated fused carbocyclic ring, which optionally contains O, N or S atoms in the ring;

in Formula II, when a=1, X is as define for Formula III, and when a=2, X is one of the following:

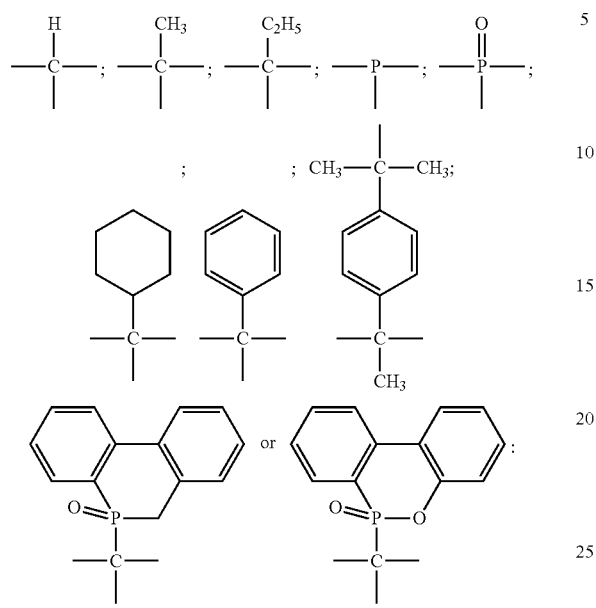

and the alkoxymethyl intermediate compound is represented by the following Formula VII:

Formula VII where x=0-10 and y=1-10; R'=H or R; R=C1-C12 straight chain, branched chain, acyclic or cyclic, saturated or unsaturated group; and Ar is the aromatic residue part of the amine of Formulas I, II or III.

2. The synthesis process of claim 1, wherein the alkyl formcel is methyl formcel.

* * * * *